US008655433B2

(12) United States Patent
Freeman et al.

(10) Patent No.: US 8,655,433 B2
(45) Date of Patent: Feb. 18, 2014

(54) HYPERSPECTRAL IMAGING IN DIABETES AND PERIPHERAL VASCULAR DISEASE

(71) Applicant: Hypermed Imaging, Inc., Greenwich, CT (US)

(72) Inventors: Jenny E. Freeman, Weston, MA (US); Svetlana Panasyuk, Lexington, MA (US); Michael Hopmeier, Mary Esther, FL (US); Kevin Schomacker, Maynard, MA (US); Derek Brand, Brighton, MA (US)

(73) Assignee: Hypermed Imaging, Inc., Greenwich, CT (US)

( * ) Notice: Subject to any disclaimer, the term of this patent is extended or adjusted under 35 U.S.C. 154(b) by 0 days.

(21) Appl. No.: 13/764,497

(22) Filed: Feb. 11, 2013

(65) Prior Publication Data
US 2013/0245455 A1    Sep. 19, 2013

Related U.S. Application Data

(63) Continuation of application No. 11/396,941, filed on Apr. 4, 2006, now Pat. No. 8,374,682.

(60) Provisional application No. 60/758,977, filed on Oct. 17, 2006, provisional application No. 60/667,677, filed on Apr. 4, 2005.

(51) Int. Cl.
*A61B 6/00* (2006.01)

(52) U.S. Cl.
USPC .......................................... 600/473; 600/476

(58) Field of Classification Search
USPC .................................................. 600/473, 476
See application file for complete search history.

(56) References Cited

U.S. PATENT DOCUMENTS

| 4,610,253 | A | 9/1986 | Rosenberg |
| 4,647,918 | A | 3/1987 | Goforth |
| 4,805,016 | A | 2/1989 | Kato |
| 4,947,850 | A | 8/1990 | Vanderkooi et al. |
| 5,088,503 | A | 2/1992 | Seitz |
| 5,349,954 | A | 9/1994 | Tiemann et al. |
| 5,438,989 | A | 8/1995 | Hochmen et al. |
| 5,539,517 | A | 7/1996 | Cabib et al. |
| 5,566,473 | A | 10/1996 | Salminen |
| 5,642,096 | A | 6/1997 | Leyerer et al. |
| 5,645,081 | A | 7/1997 | Argenta et al. |
| 5,722,287 | A | 3/1998 | Forstein |

(Continued)

FOREIGN PATENT DOCUMENTS

WO    WO 2006/058306    6/2006

OTHER PUBLICATIONS

Afromowitz et al., "Multispectral imaging of burn wounds: a new clinical instrument for evaluating burn depth." IEEE Trans Biomed Eng 1988; 35(10):842-50.

(Continued)

*Primary Examiner* — Peter Luong
(74) *Attorney, Agent, or Firm* — Brett A. Lovejoy; Andrew J. Antczak; Morgan, Lewis & Bockius, LLP

(57) ABSTRACT

The invention is directed to methods and systems of hyperspectral and multispectral imaging of medical tissues. In particular, the invention is directed to new devices, tools and processes for the detection and evaluation of diseases and disorders such as, but not limited to diabetes and peripheral vascular disease, that incorporate hyperspectral or multispectral imaging.

21 Claims, 10 Drawing Sheets

(56) References Cited

U.S. PATENT DOCUMENTS

| | | | |
|---|---|---|---|
| 5,782,770 | A | 7/1998 | Mooradian et al. |
| 5,995,645 | A | 11/1999 | Soenksen et al. |
| 6,104,939 | A | 8/2000 | Groner et al. |
| 6,122,846 | A | 9/2000 | Gray et al. |
| 6,246,301 | B1 | 6/2001 | Sogo et al. |
| 6,556,853 | B1 | 4/2003 | Cabib et al. |
| 6,587,711 | B1 | 7/2003 | Alfano et al. |
| 6,640,130 | B1 | 10/2003 | Freeman et al. |
| 6,640,132 | B1 | 10/2003 | Freeman et al. |
| 6,728,561 | B2 | 4/2004 | Smith et al. |
| 6,741,884 | B1 | 5/2004 | Freeman et al. |
| 6,750,964 | B2 | 6/2004 | Levenson et al. |
| 6,810,279 | B2 | 10/2004 | Mansfield et al. |
| 6,918,883 | B2 | 7/2005 | Horton et al. |
| 6,937,885 | B1 | 8/2005 | Lewis et al. |
| 7,013,172 | B2 | 3/2006 | Mansfield et al. |
| 7,166,852 | B2 | 1/2007 | Saracen et al. |
| 7,920,908 | B2 | 4/2011 | Hattery et al. |
| 2001/0036304 | A1 | 11/2001 | Yang et al. |
| 2002/0055092 | A1 | 5/2002 | Hochmen |
| 2002/0057431 | A1 | 5/2002 | Fateley et al. |
| 2002/0061142 | A1 | 5/2002 | Hiramatsu |
| 2002/0099295 | A1 | 7/2002 | Gil et al. |
| 2002/0154300 | A1 | 10/2002 | Mansfield et al. |
| 2002/0177894 | A1 | 11/2002 | Acosta et al. |
| 2003/0139667 | A1 | 7/2003 | Hewko et al. |
| 2004/0111030 | A1 | 6/2004 | Zeman |
| 2004/0119020 | A1 | 6/2004 | Bodkin |
| 2004/0204651 | A1 | 10/2004 | Freeman et al. |
| 2004/0209237 | A1 | 10/2004 | Flewelling et al. |
| 2004/0220477 | A1 | 11/2004 | Freeman et al. |
| 2005/0049467 | A1 | 3/2005 | Stamatas et al. |
| 2006/0241495 | A1 | 10/2006 | Kurtz |
| 2006/0247514 | A1 | 11/2006 | Panasyuk et al. |
| 2007/0024946 | A1 | 2/2007 | Panasyuk et al. |
| 2007/0038042 | A1 | 2/2007 | Freeman et al. |
| 2007/0238957 | A1 | 10/2007 | Yared |
| 2007/0268485 | A1 | 11/2007 | Polonskiy et al. |
| 2009/0216097 | A1 | 8/2009 | Wilson et al. |

OTHER PUBLICATIONS

Armstrong et al., "Predicting neuropathic ulceration with infrared dermal thermometry." J Am Podiatr Med Assoc 1997; 87(7):336-7.
Beckert et al., "The Impact of the Micro-Lightguide O2C for the Quantification of Tissue Ischemia in Diabetic Foot Ulcers." Diabetes Care 2004; 27(12):2863-2867.
Brearley et al., "Peripheral pulse palpation: an unreliable physical sign." Ann R Coll Surg Engl. May 1992; 74(3):169-71.
Caputo et al., "Assessment and management of foot disease in patients with diabetes." N Engl J Med 1994; 331 (13):85460.
Carlson et al "A historical overview and update on pulse oximetry." Anesthesiol Rev 1993; 20:173-181.
Cavanagh et al., "Correlates of structure and function in neuropathic diabetic feet," Diabetologia 1991; 34(Suppl 2):A39 (abstract).
Colarusso et al., "Infrared spectroscopic imaging: from planetary to cellular systems." Appl Spectrosc 1998; 52:106A-120A.
Dahab, G. et al, "Digital Quantification of Fibrosis in Liver Biopsy Sections: Description of a New Method by Photoshop Software", Journal of Gastroenterology and Hepatology 19:pp. 78-85, 2004.
Dinh et al. "The use of medical hyperspectral technology to evaluate microcirculatory changes in diabetic foot ulcers and predict clinical outcomes." 2007, Diabetes Care:30:903-910.
Dinh et al. "The use of Medical HyperSpectral Imaging (MHSI) to identify patients at risk for developing diabetic foot ulcers." Diabetes 2005;54(SI):A270.
Ferrara et al. "Clinical applications of angiogenic growth factors and their inhibitors". Dec. 1999. Nature Medicine. vol. 5, No. 12: 1359-1364.
Freeman et al., "'Medical hyperspectral imaging (MHSI) of 1,2-dimethylbenz(a)-anthracene (DMBA)-induced breast tumors in rats." Poster #1001. In: 27th Annual San Antonio Breast Cancer Symposium; 2004; San Antonio, Texas: Breast Cancer Research and Treatment; 2004. p. S51.
Frykberg et al. "Diabetic foot disorders: a clinical practice guideline. American College of Foot and Ankle Surgeons." J Foot Ankle Surg 2000;39(5 Suppl):SI-60.
Frykberg et al., "Role of neuropathy and high foot pressures in diabetic foot ulceration." Diabetes Care. Oct. 1998;21(10):1714-9.
Frykberg RG. "Diabetic Toot ulcers: pathogenesis and management." Am Fam Physician 2002; 66(9): 1655-62.
Gillies et al., "Systemic effects of shock and resuscitation monitored by visible hyper spectral imaging." Diabetes Technol Therapeut 2003; 5(5):847-855.
Greenman et al., "Early changes in the skin microcirculation and muscle metabolism of the diabetic foot." Lancet 2005; 366: 1711-1718.
Harrington et al., "A cost analysis of diabetic lower-extremity ulcers." Diabetes Care 2000; 23(9):1333-8.
Hittel and Donnelly, "Treating peripheral arterial disease in patients with diabetes," Diabetes Obes Metab 2002; 4 Suppl 2:S26-31.
Johnson, William R., et al., Snapshot Hyperspectral imaging in Ophthalmology, Journal of Biomedical Optics 12(1), 014036 (Jan./Feb. 2007).
Khan and Newton, "Laser Doppler imaging in the investigation of lower limb wounds." Int J Low Extrem Wounds 2003;2(2):74-86.
Lavery and Gazewood. "Assessing the feet of patients with diabetes." J Fam Pract 2000;49(11 Suppl):S9-6.
Lavery et al., "Practical criteria for screening patients at high risk for diabetic foot ulceration." Arch Intern Med 1998;158(2):157-62.
Martinez, Luis. "A Non-invasive spectral reflectance method for mapping blood oxygen saturation in wounds". Proceedings of the 31st Applied Imagery Pattern Recognition Workshop 2002; p. 1112.
McMillan DE, "Development of vascular complications in diabetes." Vasc Med 1997; 2(2): 132-42.
Daisuke, Nakao et al., 'Real time multi spectral image processing for mapping pigmentation in human skin' Med Imaging Technol vol. 20, No. 2, 2002, pp. 123-133, XP008142850.
Novo S. "Classification, epidemiology, risk factors, and natural history of peripheral arterial disease." Diabetes Obes Metab 2002; 4 Suppl 2:S1-6.
Palumbo et al., "Peripheral vascular disease and diabetes." In: Harris et al. (editors). *Diabetes in America*, 1st ed, Washington, DC: US Government Printing Office; 1985.
Payette et al., "Noninvasive diagnostics: predicting flap viability with near-IR spectroscopy and imaging," Am Clinical Laboratory 1999; 18:4-6.
Pecoraro et al, "Pathways to diabetic limb amputation. Basis for prevention." Diabetes Care 1990; 13(5):513-21.
Rajbhandari et al., Early identification of diabetic foot ulcers that may require intervention using the micro lightguide spectrophotometer, Diabetes Care 1999;22(8): 1292-1295.
Ramsey et al. "Incidence, outcomes, and cost of foot ulcers in patients with diabetes." Diabetes Care 1999; 22(3):382-7.
Reiber et al., "Lower extremity foot ulcers and amputations in diabetes." In: Harris et al. (editors). *Diabetes in America*. 2nd ed. Washington, DC: US Government Printing Office; 1995. p, 402-428.
Riaza et al., "Spectral mapping of rock weathering degrees on granite using hyper spectral DAIS 7915 Spectrometer Data." Internl J Applied Earth Observation and Geoinformation Special issue; Applications of imaging spectroscopy 2001;3-4:345-354.
Sheffield et al "Laser Doppler Flowmetry." In: *Wound Care Practice*. Flagstaff , AZ. Best Publishing Company; 2004, p. 137.
Sowa et al., "Near infrared spectroscopic assessment of hemodynamic changes in the early post-bum period." Bums 2001;27:241-249.
Sumplo BE. "Foot ulcers." N Engl J Med. Sep. 14, 2000;343(11):787-93.
Sykes and Godsey, "Vascular evaluation of the problem diabetic foot." Clin Podiatr Med Surg 1998; 15(1):49-83.
Thenkabail et al., "Hyperspectral vegetation indices and their relationships with agricultural crop characteristics," Remote Sens Environ 2000;71 (Remote Sens Environ): 158-182.

(56) References Cited

OTHER PUBLICATIONS

Treado et al., "Infrared and Raman spectroscopic imaging," Appl Spectrosc Rev 1994;29: 1-38.

van der Laak et al, "Hue-Saturation-Density (HSD) Model for Stain Recognition in Digital imagines from Transmitted Light Spectroscopy" Cytometry 39:pp. 275-284, 2000.

Veves et al. "The Use of Medical HyperSpectral Imaging (MHSI) to evaluate microcirculatory changes and predict clinical outcomes: application to diabetic foot ulcers." Society of Vascular Medicine and Biology 17th Annual Scientific Session 2006(abstract).

Wardlaw et al, "Imaging appearance of the symptomatic perforating artery in patients with lacunar infarction: occlusion or other vascular pathology?", Ann Neurol 2001;50(2):208-15.

Young et al., "The prediction of diabetic neuropathic foot ulceration using vibration perception thresholds. A prospective study." Diabetes Care 1994; 17(6):557-60.

Zamboni et al. "Evaluation of hyperbaric oxygen for diabetic wounds: a prospective study", Undersea Hyper Med 1997; 24(3):175-179.

Zimny et al., "Early detection of microcirculatory impairment in diabetic patients with foot at risk." Diabetes Care 2001; 24(10): 1810-4.

Zuzak et al. "Noninvasive determination of spatially resolved and time-resolved tissue perfusion in humans during nitric oxide inhibition and inhalation by use of a visible-reflectance hyper spectral imaging technique." Circulation 2001; 104:2905-2910.

Mak et al, "State-of-the-art research in lower-limb prosthetic biomechanics-socket interface: a review.", J Rehabil Res Dev. Mar.-Apr. 2001;38(2):161-74.

HYPERSPECTRAL IMAGING IN DIABETES AND PERIPHERAL VASCULAR DISEASE

REFERENCE TO RELATED APPLICATIONS

The present application is a continuation of U.S. patent application Ser. No. 11/396,941, filed Apr. 4, 2006, which claims priority to U.S. Provisional Patent Application Ser. No. 60/667,677 entitled Hyperspectral Imaging in Diabetes, filed Apr. 4, 2005, and U.S. Provisional Patent Application Ser. No. 60/785,977 entitled Hyperspectral Imaging of Angiogenesis, filed Mar. 27, 2006, all which are hereby incorporated by reference.

BACKGROUND

1. Field of the Invention

The invention is directed to methods and systems of hyperspectral and multispectral imaging of medical tissues. In particular, the invention is directed to new devices, tools and processes for the detection and evaluation of diseases and disorders such as diabetes and peripheral vascular disease that incorporate hyperspectral/multispectral imaging.

2. Background of the Invention

Diabetes afflicts an estimated 194 million people worldwide, affecting 7.9% of Americans (over 21 million people) and 7.8% of Europeans. Between 85% and 95% of all diabetics suffer from Type 2 diabetes, although nearly 5 million people worldwide suffer from Type 1 diabetes, affecting an estimated 1.27 million people in Europe and another 1.04 million people in the United States[1]. Both Type 1 and Type 2 diabetic patients are at higher risk for a wide array of complications including heart disease, kidney disease (e.g. nephropathy), ocular diseases (e.g. glaucoma), and neuropathy and nerve damages to name a few[2]. The feet of diabetic patients are at risk for a wide array of complications, which are discussed below. Problems with the foot that affect the ambulatory nature of the patient are not only important from the standpoint of physical risk, but also convey an emotional risk as well, as these problems disrupt the fundamental independence of the patient by limiting his or her ability to walk.

Peripheral arterial disease (PAD) affects primarily people older than 55. There are currently 59.3 million Americans older than 55, and over 12 million of them have symptomatic peripheral vascular disease. It is estimated that only 20% of all patients with PAD have been diagnosed at this time. This represents a dramatically underpenetrated market. Although pharmacologic treatments for PAD have traditionally been poor, 2.1 million nevertheless receive pharmacologic treatment for the symptoms of PAD, and current diagnostic tests are not considered to be very sensitive indicators of disease progression or response to therapy. Additionally, 443,000 patients undergo vascular procedures such as peripheral arterial bypass surgery (100,000) or peripheral angioplasty (343,000) annually and are candidates for pre and post surgical testing. One difficulty in diagnosing PAD is that in the general population, only about 10% of persons with PAD experience classic symptoms of intermittent claudication. About 40% of patients do not complain of leg pain, while the remaining 50% have leg symptoms which differ from classic claudication.

Relying on medial history and physical examination alone is unsatisfactory. In one study, 44 percent of PAD diagnoses were false positive and 19 percent were false negative when medical history and physical examination alone were used.[3] For this reason, physicians have looked for other means to help in providing diagnosis. As in the case of diabetic foot disease, current technologies have fallen short. Nonetheless, patients are frequently sent to peripheral vascular laboratories for non-invasive studies. While the test results are known to be inaccurate, these results do provide some additional information to physicians for assistance in diagnosis or treatment decisions.

Another problem face by physicians is disease of the peripheral veins. Venous occlusive disease due to incompetent valves in veins designed to prevent backflow and deep vein thrombosis, results in venous congestion and eventually stasis ulcers. Approximately 70% of leg ulcers are due to venous occlusion. Many of these ulcers are found at the medial malleolus. The foot is generally swollen and the skin near the ulcer site is brownish in appearance.

Pathology

Diabetic feet are at risk for a wide range of pathologies, including microcirculatory changes, peripheral vascular disease, ulceration, infection, deep tissue destruction and metabolic complications. The development of an ulcer in the diabetic foot is commonly a result of a break in the barrier between the dermis of the skin and the subcutaneous fat that cushions the foot during ambulation. This, in turn, can lead to increased pressure on the dermis, resulting in tissue ischemia and eventual death, and ultimately result in an ulcer.[4] There are a number of factors that weigh heavily in the process of ulcerations[5]—affecting different aspects of the foot—that lead to a combination of effects that greatly increase the risk of ulceration:[6]

Neuropathy—Results in a loss of protective sensation in the foot, exposing patients to undue, sudden or repetitive stress. Can cause a lack of awareness of damage to the foot as it be occurs and physical defects and deformities[7] which lead to even greater physical stresses on the foot. It can also lead to increased risk of cracking and the development of fissures in calluses, creating a potential entry for bacteria and increased risk of infection.[8]

Microcirculatory Changes—Often seen in association with hyperglycemic damage.[9] Functional abnormalities occur at several levels, including hyaline basement membrane thickening and capillary leakage. On a histologic level, it is well known that diabetes causes a thickening of the endothelial basement membrane which in turn may lead to impaired endothelial cell function.

Musculoskeletal Abnormalities—Include altered foot mechanics, limited joint mobility, and bony deformities, and can lead to harmful changes in biomechanics and gait. This increases pressures associated with various regions of the foot. Alteration or atrophy of fat pads from increased pressure can lead to skin loss or callus, both of which increase the risk of ulceration by two orders of magnitude.

Peripheral Vascular Disease—Caused by atherosclerotic obstruction of large vessels resulting in arterial insufficiency[10] is common in the elderly populations and is yet more common and severe in diabetics.[11] Diabetics may develop atherosclerotic disease of large-sized and medium-sized arteries, however, significant atherosclerotic disease of the infrapopliteal segments is particularly common. The reason for this is thought to result from a number of metabolic abnormalities in diabetics, including high LDL and VLDL levels, elevated plasma von Willebrand factor, inhibition of prostacyclin synthesis, elevated plasma fibrinogen levels, and increased platelet adhesiveness.

Venous Disease—Caused by incompetent valves controlling backflow between the deep veins and the more superficial veins or thrombosis of the deep veins. Venous occlusions are typically observed in the elderly who typically presented with swollen lower extremities and foot ulcers typically at the medial malleolus.

Previous studies have shown that a foot ulcer precedes roughly 85% of all lower extremity amputations in diabetic patients[12,13] and that 15% of all diabetic patients will develop a foot ulcer during the course of their lifetimes.[14] More than 88,000 amputations performed annually on diabetics,[15] and roughly an additional 30,000 amputations are performed on nondiabetics, mostly related to peripheral vascular disease. Estimations have shown that between 2-6% of diabetic patients will develop a foot ulcer every year[13,16] and that the attributable cost for an adult male between 40 and 65 years old is over $27,000 (1995 US dollars) for the two years after diagnosis of the foot ulcer.[16] In conjunction with the increased total costs of care, Ramsey et al showed that diabetic patients incurred more visits to the emergency room (more than twice as many as control patients), more outpatient hospital visits (between 2× and 3× as many as control subjects) and more inpatient hospital days (between 3× and 4× as many as control patients) during the course of an average year.

Foot pathology is major source of morbidity among diabetics and is a leading cause of hospitalization. The infected and/or ischemic diabetic foot ulcer accounts for about 25% of all hospital days among people with diabetes, and the costs of foot disorder diagnosis and management are estimated at several billion dollars annually.[16, 17]

Current Diagnostic Procedures

The first step in the assessment of the diabetic foot is the clinical examination[18, 19]. All patients with diabetes require a thorough pedal examination at least once a year, even without signs of neuropathy. Evaluation of the diabetic patient with peripheral vascular disease should include a thorough medical history, vascular history, physical examination, neurologic evaluation for neuropathy and a thorough vascular examination.[20]

The next step in the work up of a patient with significant peripheral vascular or diabetic foot disease is non-invasive testing.[21] Current clinical practice can include ankle brachial index (ABI), transcutaneous oxygen measurements (TcPO2), pulse volume recordings (PVR) and laser Doppler flowmetry. All of these clinical assessments are highly subjective with significant inter- and intra-observer variability especially in longitudinal studies. None of these methods are discriminatory for feet at risk, and none of them provide any information about the spatial variability across the foot. Doppler ultrasound with B-mode realtime imaging is typically used to diagnose deep vein thrombosis while photo and air plethysmography are used to measure volume refill rates as a means of locating and diagnosing valvular insufficiency. Currently there is no method to accurately assess the predisposition to serious foot complications, to define the real extent of disease or to track the efficacy of therapeutics over time.

SUMMARY OF INVENTION

The present invention overcomes the problems and disadvantages associated with current strategies and designs, and provides new tools and methods for detecting tissue at risk of developing into an ulcer, for detecting problems with diabetic foot disease, and for evaluating the potential for wounds to heal.

One embodiment of the invention is directed to a medical instrument comprising a first stage optic responsive to illumination of tissue, a spectral separator, one or more polarizers, an imaging sensor, a diagnostic processor, a filter control interface, a general purpose operating module to assess the state of tissue in diabetic subjects following a set of instructions, and a calibrator. Preferably, the instrument further comprises a second stage optic responsive to illumination of tissue. Preferably, the set of instructions comprises preprocessing hyperspectral information, building a visual image, defining a region of interest in tissue, converting the visual image into units of optical density by taking a negative logarithm of each decimal base, decomposing a spectra for each pixel into several independent components, determining three planes for an RGB pseudo-color image, determining a sharpness factor plane, converting the RGB pseudo-color image to a hue-saturation-value/intensity image having a plane, adjusting the hue-saturation-value/intensity image plane with the sharpness factor plane, converting the hue-saturation-value/intensity image back to the RGB pseudo-color image, removing outliers beyond a standard deviation and stretching image between 0 and 1, displaying the region of interest in pseudo-colors; and characterizing a metabolic state of the tissue of interest.

Preferably, the region of interest is one of a pixel, a specified region or an entire field of view. Preferably, determining three planes for an RGB pseudo-color image comprises one or more characteristic features of the spectra, determining a sharpness factor plane comprises a combination of the images at different wavelengths, removing outliers beyond a standard deviation comprises three standard deviations, displaying the region of interest in pseudo-colors comprises one of performing one in combination with a color photoimage of a subject, in addition to a color photo image of a subject, and projecting onto the tissue of interest.

Preferably, defining the color intensity plane as apparent concentration of one or a mathematical combination of oxygenated Hb, deoxygenated Hb, and total Hb, oxygen saturation, defining the color intensity plane as reflectance in blue-green-orange region, adjusting the hue saturation comprises adjusting a color resolution of the pseudo-color image according to quality of apparent concentration of one or a mathematical combination of oxygenated Hb, deoxygenated Hb, and total Hb, oxygen saturation, adjusting the hue saturation further comprises one or a combination of reducing resolution of hue and saturation color planes by binning the image, resizing the image, and smoothing the image through filtering higher frequency components out, and further interpolating the smoothed color planes on a grid of higher resolution intensity plane.

Another embodiment of the invention is directed to a method for assessing the state of tissue of a diabetic subject comprising, preprocessing hyperspectral information, building a visual image, defining a region of interest in tissue, converting the visual image into units of optical density by taking a negative logarithm of each decimal base, decomposing a spectra for each pixel into several independent components, determining three planes for an RGB pseudo-color image, determining a sharpness factor plane, converting the RGB pseudo-color image to a hue-saturation-value/intensity image having a plane, adjusting the hue-saturation-value/intensity image plane with the sharpness factor plane, converting the hue-saturation-value/intensity image back to the RGB pseudo-color image, removing outliers beyond a standard deviation and stretching image between 0 and 1, displaying the region of interest in pseudo-colors; and characterizing a metabolic state of the tissue of interest.

Preferably, the region of interest is one of a pixel, a specified region or an entire field of view. Preferably, determining three planes for an RGB pseudo-color image comprises one or more characteristic features of the spectra, determining a sharpness factor plane comprises a combination of the images at different wavelengths, removing outliers beyond a standard deviation comprises three standard deviations, displaying the region of interest in pseudo-colors comprises one of performing one in combination with a color photoimage of a subject, in addition to a color photo image of a subject, and projecting onto the tissue of interest.

Preferably, defining the color intensity plane as apparent concentration of one or a mathematical combination of oxygenated Hb, deoxygenated Hb, and total Hb, oxygen saturation, defining the color intensity plane as reflectance in blue-green-orange region, adjusting the hue saturation comprises adjusting a color resolution of the pseudo-color image according to quality of apparent concentration of one or a mathematical combination of oxygenated Hb, deoxygenated Hb, and total Hb, oxygen saturation, adjusting the hue saturation further comprises one or a combination of reducing resolution of hue and saturation color planes by binning the image, resizing the image, and smoothing the image through filtering higher frequency components out, and further interpolating the smoothed color planes on a grid of higher resolution intensity plane.

Other embodiments and advantages of the invention are set forth in part in the description, which follows, and in part, may be obvious from this description, or may be learned from the practice of the invention.

DESCRIPTION OF THE INVENTION

Background of Hyperspectral Imaging

Figure 1:
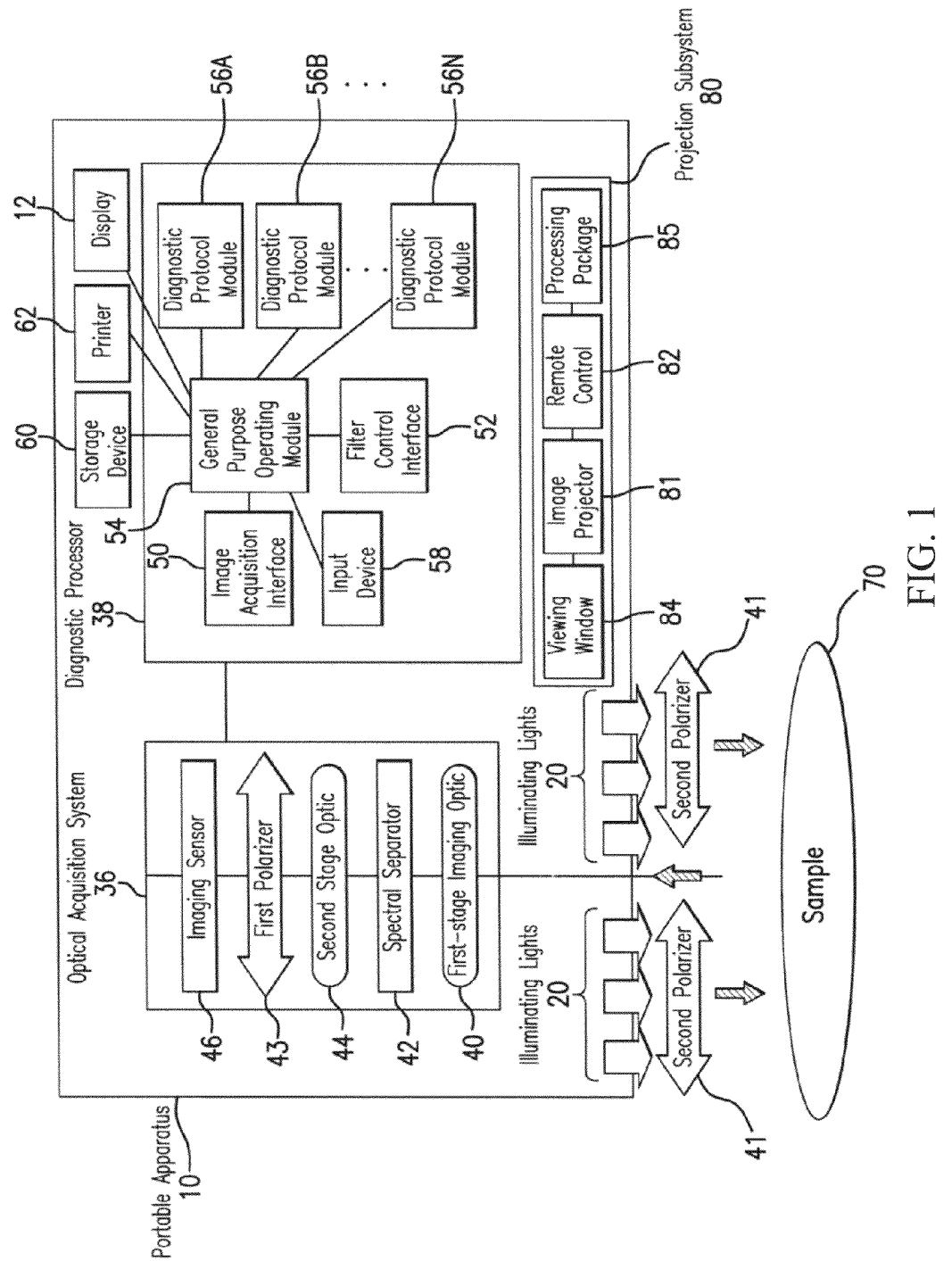
FIG. 1: Block diagram depicting a portable hyperspectral imaging apparatus.

HSI or hyperspectral imaging is a novel method of "imaging spectroscopy" that generates a "gradient map" of a region of interest based on local chemical composition. HSI has been used in satellite investigation of suspected chemical weapons production areas[22], geological features[23], and the condition of agricultural fields[24] and has recently been applied to the investigation of physiologic and pathologic changes in living tissue in animal and human studies to provide information as to the health or disease of tissue that is otherwise unavailable.[25] MHSI for medical applications (MHSI) has been shown to accurately predict viability and survival of tissue deprived of adequate perfusion, and to differentiate diseased (e.g. tumor) and ischemic tissue from normal tissue.[27]

Spectroscopy is used in medicine to monitor metabolic status in a variety of tissues. One of the most common spectroscopic applications is in pulse oximetry, which utilize the different oxyhemoglobin (oxyHb) and deoxyhemoglobin (deoxyHb) absorption bands to estimate arterial hemoglobin oxygen saturation.[28] One of the drawbacks of these systems is that they provide no information about the spatial distribution or heterogeneity of the data. In addition, these systems report the ratio of oxyHb and deoxyHb together losing diagnostic information that can be garnered by evaluating the state of the individual components. Such spatial information for the individual components and the ratio is provided by HSI, which is considered a method of "imaging spectroscopy", where the multi-dimensional (spatial & spectral) data are represented in what is called a "hypercube." The spectrum of reflected light is acquired for each pixel in a region, and each such spectrum is subjected to standard analysis. This allows the creation of an image based on the metabolic state of the region of interest (ROI).

In vivo, MHSI has been used to demonstrate otherwise unobserved changes in pathophysiology. Specific studies have evaluated the macroscopic distribution of skin oxygen saturation,[29] the in-situ detection of tumor during breast cancer resection in the rat,[27] the determination of tissue viability following plastic surgery & burns,[30, 31] claudication and foot ulcers in diabetic patients,[32-37] and applications to shock and lower body negative pressure (LBNP) in pigs and humans, respectively.[38-40] In a skin pedicle flap model in the rat, tissue that has insufficient oxygenation to remain viable is readily apparent from local oxygen saturation maps calculated from hyperspectral images acquired immediately following surgery; by contrast, clinical signs of impending necrosis do not become apparent for 12 hours after surgery.[41]

Non-invasive measurements of oxygen or blood flow have been demonstrated previously, with investigators using thermometry,[42] point diffuse reflectance spectroscopy,[43, 44] and laser Doppler imaging.[45] Sheffield et al, have also reviewed laser Doppler and TcPO2 measurements and their specific applications to wound healing.[46] While other techniques have been utilized in both the research lab and the clinic and have the advantage of a longer experience base, MHSI is superior to other technologies and can provide predictive information on the onset and outcomes of diabetic foot ulcers, venous stasis ulcers and peripheral vascular disease.

Because MHSI has the ability to show anatomically relevant information that is useful in the assessment of local, regional and systemic disease. This is important in the assessment of people with diabetes and/or peripheral vascular disease. MHSI shows the oxygen delivery and oxygen extraction of each pixel in the image collected. These images with pixels ranging from 20 microns to 120 microns have been useful in several ways. In the case of systemic disease, MHSI shows the effects on the microcirculation of systemic diabetes, smoking, a variety of medications such as all of the classes of antihypertensives (ACE inhibitors, ARBs, Beta blockers, Peripheral arterial and arteriolar dilators), vasodilators (such as nitroglycerine, quinine, morphine), vasoconstrictors (including coffee, tobacco, pseudephedrine, Ritalin, epinephrine, levophedrine, neosynepherine), state of hydration, state of cardiac function (baseline, exercise, congestive heart failure), systemic infection or sepsis as well as other viral or bacterial infections and parasitic diseases. The size of the pixels used is important in that it is smaller than the spacing of the perforating arterioles (~0.8 mm)[47] of the dermis and therefore permits the visualization of the distribution of mottling or other patterns associated with the anatomy of the microcirculation and its responses. In the case of the use of MHSI for regional assessment, in addition to the above systemic effects at play, the image delivers information about the oxygen delivery and oxygen extraction for a particular region as it is influenced by blood flow through the larger vessels of that region of the body. For example an image of the top of the foot reflects both the systemic microvascular status and the status of the large (macrovascular) vessels supplying the leg. This can reflect atherosclerotic or other blockage of the vessel, potential injury to the vessel with narrowing, or spasm of some of the smaller vessels. It can also reflect other regionalized processes such as neuropathy or venous occlusion or compromise or stasis. In the case of local disease MHSI shows the actual effect of the combination of systemic, regional and local effects on small pieces of tissue. This combines the effects of systemic and regional effects described above with the effects of local influences on the tissue including pressure, neuropathy, localized small vessel occlusion, localized trauma or wounding, pressure sore, inflammation, and wound healing. Angiogenesis during wound healing is readily monitored with MHSI.

Wounds other than on the foot can be similarly assessed, such as sacral decubiti, other areas of pressure necrosis, prosthesis stumps, skin flap tissue before, after or during surgery, areas of tissue breakdown after surgery, and burn injuries. Current optical methods for evaluating tissues for the conditions described above include:

Laser Doppler (LD)—In early iontophoresis experiments as well as recent efforts both LD and MHSI data were collected, and some changes in our images (total hemoglobin) are primarily a consequence of changes in perfusion which was roughly correlated to LD. However, important other changes in MHSI images that report specifically $O_2$ extraction and tissue metabolism (O2Sat) are not related to perfusion or LD readings per-se. Superior spatial resolution with MHSI, and $O_2$ extraction information adds highly important clinical information.

Transcutaneous $PO_2$ ($TcPO_2$)—$TcPO_2$ data collected in subjects with peripheral vascular disease and ischemia study as well as in patients with diabetes both with and without foot ulcers. $TcPO_2$ measurements appeared cumbersome, lengthy (~20-30 minutes), highly operator dependant, and carried data only from skin directly under the probe (with little ability to distinguish the spatial characteristics of the ischemic area). While $TcPO_2$ has been shown to carry statistically significant information in terms of quantifying tissue at risk for ulceration,[48] $TcPO_2$ was not encouraging as a useful clinical device.

Non-imaging techniques—Techniques such as near-infrared absorption spectroscopy (NIRS) or $TcPO_2$, rely on measurements at a single point in tissue which may not accurately reflect overall tissue condition or provide anatomically relevant data, and probe placement on the skin can alter blood flow and cannot deliver accurate information in the area of an ulcer or directly surrounding it. Because MHSI is truly remote sensing, data are acquired at a distance, eliminating probe placement errors and allowing the investigation of the wound itself, which some techniques can not accomplish due to infection risk.

In short, analysis of the present invention supports the following conclusions:

1. Level of oxygenated hemoglobin in the tissue of arms and feet of diabetic subjects is lower than the level of oxygenated hemoglobin in the skin of control subjects. This is statistically significant result with separation between diabetics and controls.[36]
2. Oxyhemoglobin in the arms and feet of ulcerated subjects is lower than oxyhemoglobin in diabetics without the ulceration. The strong signal suggests ability to distinguish diabetics at lower and high risk.
3. Oxygen saturation level in the skin of arms and feet of diabetics is lower than oxygen saturation in the skin of controls. This is at a statistically significant level allowing separation between diabetics and controls.
4. MHSI quantitatively assesses different areas of tissue metabolism on both dorsal and plantar foot surfaces of any curvature.
5. MHSI evaluates state of tissue as a function of distance away from ulcer to assess the viability of surrounding tissue, and evaluate the degree of risk of further ulceration.
6. MHSI can be classified with a 4-quadrant system to determine the metabolic state of tissue using oxygen delivery and oxygen extraction: low/low, low/high, high/high, and high/low. This metric is used in distinguishing healthy tissue from ulcerated, or from a tissue at risk of ulceration.
7. MHSI is a unique visualization method that produces an image that combines spatial information from three independent parameters characterizing tissue: oxygenated and deoxygenated hemoglobin concentrations and light absorption.
8. MHSI evaluates skin metabolism at high resolution of 20-120 microns per image pixel.
9. Specific MHSI regions associated with the margins of the ulcer correlate to inflammation (and/or infection).
10. Areas of decreased MHSI indicate tissue at risk for non-healing, ulcer extension, or primary ulceration.

11. MHSI differentiates between regions of tissue associated with a present foot ulcer on the basis of biomarkers such as oxyHb and deoxyHb coefficients.
12. MHSI evaluates temporal changes in oxygen delivery and extraction to particular areas, both, on local and systemic scale. The trend in the change of oxyHb and deoxyHb are used to predict healing status of a wound/ulcer as well as progression of diabetic complications.
13. Specific results from MHSI are indicative of inflamed tissue.
14. MHSI examines tissue for gross features that may be indicative of global risks of complications, such as poor perfusion or the inability of the microcirculation to react and compensate in tissue.
15. MHSI has potential in diagnosing global microcirculatory insufficiencies and impacting on other complications of diabetes associated with the microvasculature besides foot ulcers.

MHSI is superior to other modalities for assessing the healing potential of tissue adjacent to ulcers. MHSI provides more direct measurements of oxyHb and deoxyHb activities of the affected tissue. Hence, the discrimination is not markedly improved by adding iontophoresis results to refine prediction as is required for Laser Doppler to do so. MHSI has significant advantages over laser Doppler and $TcPO_2$ measurements. Whereas MHSI is able to deliver spatially relevant data with high spatial resolution, $TcPO_2$ delivers only single point data. Laser Doppler data has poor spatial resolution and is frequently reported as a single mean numerical value across the region of interest.

The major clinical advantage of hyperspectral imaging is the delivery of metabolic information derived from the tissue's spectral properties in an easily interpretable image format with high spatial resolution. This 2-D information allows gradients in biomarker levels to be assessed spatially. Multiple images taken over time allow the gradiant to be measured temporally. This adds new dimensions to the assessment of ulceration risk and tissue healing in that it will allow the physician to target therapy and care to specific at risk areas much earlier than previously possible. The reporting of biomarkers such as oxyHb and deoxyHb levels in tissue individually and in an image format where spatial distributions can be assessed has not been done before. Typically the two numbers are combined in a ratio and reported as percent hemoglobin oxygen saturation ($O_2Sat$). MHSI has the clear potential to be developed into a cost effective, easy to use, turn-key camera-based metabolic sensor given the availability and relatively low price of components.

Surprisingly, MHSI information according to this invention can be used to predict the onset of foot ulcers before there are clinical indications, and provides early detection, diagnosis, and quantification of progression of microcirculatory complications such as neuropathy in diabetic patients. For patients with foot ulcers, MHSI technology can evaluate the ulcer and surrounding area to predict whether that will heal or require surgical intervention. The present invention also provides MHSI that is useful in the prediction and monitoring of peripheral venous disease including venous ulcers.

There are many advantages to using MHSI. Not only does MHSI provide anatomically relevant spectral information, its use of spectral data of reflected electro-magnetic radiation (ultraviolet—UV, visible, near infrared—NIR, and infrared—IR) provides detailed tissue information. Since different types of tissue reflect, absorb, and scatter light differently, in theory the hyperspectral cubes contain enough information to differentiate between tissue types and conditions. MHSI is more robust than conventional analyses since it is based on a few general properties of the spectral profiles (slope, offset, water, oxyHb, deoxyHb, and its ratio) and is therefore flexible with respect to spectral coverage and not sensitive to a particular light wavelength. MHSI is faster than conventional analyses because it uses fast image processing techniques that allow superposition of absorbance, scattering, and oxygenation information in one pseudo-color image. Visible MHSI is useful because it clearly depicts oxyHb and deoxyHb which are important, physiologically relevant biomarkers in a spatially relevant fashion. Similarly, NIR shows water, oxyHb and deoxyHb.

The simplicity of the presented false color images representing distribution of various chemical species, either singly or in combination (such as ratioed), or in other more sophisticated image processing techniques allow for the display of results in real to near-real time. Another advantage of MHSI is easy interpretation. Color changes show the different tissue types or condition, but the distinction is not a yes/no type. MHSI color scheme allows the surgeon or podiatrist to differentiate between different tissue types and states. In addition, the color and the shape of structures depict different composition and level of viability of the tissue. The data is then represented in a developed MHSI standard format. OxyHb and deoxyHb are presented in a format similar to a blood pressure reading that is easy for physicians to understand. Additionally, a tissue oxygen saturation value denoted as $S_{HSI}O_2$ is also provided.

MHSI main purposes include[1] expand human capabilities beyond the ordinary array of senses; 2) expand the human brain capabilities by pre-analyzing the spectral characteristics of the observable subject; 3) perform these tasks with real or near-real time data acquisition. In summary, the aim of MHSI is to facilitate the diagnosis and assessment of the metabolic state of tissue.

Results of analysis have to be presented in an easily accessible and interpretable form. MHSI delivers results in an intuitive form by pairing MHSI pseudo-color image with a high quality color picture composed from the same hyperspectral data. Identification and assessment of a region of interest (ROI) is easily achieved by flipping between color and MHSI images, and zooming onto the ROI. The images can be seen on a computer screen or projector, and/or stored and transported as any other digital information, and/or printed out. The MHSI image preserves the high resolution of the hyperspectral imager thereby allowing further improvement with upgraded hardware.

Additionally, MHSI transcribes vast 3D spectral information sets into one image preserving biological complexity via millions of color shades. The particular color and distinct shape of features in the pseudo-color image allow discrimination between tissue types such as ulcers, callus, intact skin, hematoma, and superficial blood vessels.

Initially, the algorithm presents oxyHb, deoxyHb and $S_{HSI}O_2$ to the user to conclude characteristics of the tissue including, but not limited to, discerning whether the tissue is healing or whether it is at a high risk of ulceration. In another embodiment, a particular color code contains adequate information for diagnosis and is presented as such. In one iteration, MHSI by itself is not a definite decision making algorithm; it is a tool that a medical professional can use in order to give a confident diagnosis. In another iteration, MHSI contains a decision making algorithm that provides the physician with a diagnosis.

Due to the complexity of the biological system, medical personnel desire as much information as possible in order to make the most-reliable diagnosis. MHSI provides currently unavailable information to the doctor, preferably to be used in conjunction with other clinical assessments to provide an accurate diagnosis. MHSI provides images for further analysis by the user. As more information is gathered, a spectral library is preferably compiled to allow MHSI to be a true diagnostic device.

MHSI is preferably used to quantify medical therapies in order to measure the effectiveness of new therapeutic agents or procedures. For example, in wound healing studies, a typical subject population can be broken down into one of three groups: those that will heal independent of therapy, those that will not heal independent of therapy, and the borderline cases that may benefit from the therapy. MHSI preferably is used to select borderline subjects for these studies where the treatment if effective most likely benefits the subject. MHSI is used to quantify wound progression or prevention in order to identify new therapeutic agents and to develop individual therapeutic regiments depending on subject response.

One embodiment of the invention is directed to a medical instrument comprising a first-stage optic responsive to illumination of a tissue, a spectral separator, one or more polarizers, an imaging sensor, a diagnostic processor, a filter control interface, and a general-purpose operating module (FIG. 1). Preferably, the spectral separator is optically responsive to the first-stage optic and has a control input, the polarizer filters a plurality of light beams into a plane of polarization before entering the imaging sensor, the imaging sensor is optically responsive to the spectral separator and has an image data output, the diagnostic processor comprises an image acquisition interface with an input responsive to the imaging sensor and one or more diagnostic protocol modules wherein each diagnostic protocol module contains a set of instructions for operating the spectral separator and for operating the filter control interface, the filter control interface comprises a control output provided to the control input of the spectral separator, which directs the spectral separator independently of the illumination to receive one or more wavelengths of the illumination to provide multispectral or hyperspectral information as determined by the set of instructions provided by the one or more diagnostic protocol module, and the general-purpose operating module performs filtering and acquiring steps one or more times depending on the set of instructions provided by the one or more diagnostic protocol modules.

The instrument may also comprise a second-stage optic responsive to illumination of the tissue. Preferably, the one or more wavelengths of illumination are one or a combination of UV, visible, NIR, and IR. In preferred embodiments, the multispectral or hyperspectral information determines one or more of the metabolic state of tissue to assess areas at high risk of developing into a foot ulcer or other wounded tissue to assess the potential of an ulcer or the tissue to heal. Preferred embodiments include multispectral or hyperspectral information gathered remotely and noninvasively. Alternatively, an imaging system could be affixed to a wounded area to track its progress over time. Such a system could be attached to or embedded in a dressing, skin covering or a device used to impact wound healing or maintain tissue integrity such as a vacuum suction system or a bed upon which a patient is lying or a shoe, boot or offloading device.

Another embodiment is directed to the set of instructions comprising: preprocessing the hyperspectral information, building a visual image, defining a region of interest of the tissue, converting all hyperspectral image intensities into units of optical density by taking a negative logarithm of each decimal base, decomposing a spectra for each pixel into several independent components, determining three planes for an RGB pseudo-color image, determining a sharpness factor plane, converting the RGB pseudo-color image to a hue-saturation-value/intensity (HSV/I) image having a plane, scaling the hue-saturation-value/intensity image plane with the sharpness factor plane, converting the hue-saturation-value/intensity image back to the RGB pseudo-color image, removing outliers beyond a standard deviation and stretching image between 0 and 1, displaying the region of interest in pseudo-colors; and characterizing a metabolic state of the tissue of interest.

The region of interest may be a pixel, a group of pixels in a prespecified region of a prespecified shape or a handoutlined shape or an entire field of view. Preferably, determining the three planes for an RGB pseudo-color image comprises one or more characteristic features of the spectra. Preferably, determining a sharpness factor plane comprises a combination of the images at different wavelengths, preferably by taking a ratio of a yellow plane in the range of about 550-580 nm to a green plane in the range of about 495-525 nm, or by taking a combination of oxyHb and deoxyHb spectral components, or by taking a ratio between a wavelength in the red region in the range 615-710 nm and a wavelength in the yellow region in the range of about 550-580 nm or in the orange region in the range of about 580-615 nm. Preferably, outliers are removed beyond a standard deviation, preferably three standard deviations. The region of interest is displayed in pseudo-colors, performed with one of in combination with a color photo image of a subject, or in addition to a color photo image of a subject, or by projecting the pseudo-color image onto the observed surface.

Another embodiment of the invention is directed to a method for evaluating DFU or area of tissue at risk comprising preprocessing the hyperspectral information, building a visual image, defining a region of interest of the tissue, converting all hyperspectral image intensities into units of optical density by taking a negative logarithm of each decimal base, decomposing a spectra for each pixel into several independent components, determining three planes for an RGB pseudo-color image, determining a sharpness factor plane, converting the RGB pseudo-color image to a hue-saturation-value/intensity (HSV/I) image having a plane, scaling the hue-saturation-value/intensity image plane with the sharpness factor plane, converting the hue-saturation-value/intensity image back to the RGB pseudo-color image, removing outliers beyond a standard deviation and stretching image between 0 and 1, displaying the region of interest in pseudo-colors, and characterizing a metabolic state of the tissue of interest.

Another embodiment is directed to a medical instrument comprising an image projector, an illumination source, a remote control device and a real-time data processing package. Such a system could project the colorized or other kind of image with relevant information back onto the tissue from which it was taken to assist the physician in diagnosis and treatment such as wound debridement. Alternatively, information can be transmitted to the physician using multiple means, one of such can be a heads-up display.

Another embodiment is intended to help tell the doctor level of amputation, safety of debriding tissue, likelihood for tissue to heal, selection and monitoring of specific therapy including topical pharmaceuticals, skin-like coverings, vacuum suction apparatus, systemic pharmaceuticals, adequacy of surgical, stenting or atherectomy procedure, extension of infection vs inflammation of tissue to assist in therapy, identification of organism responsible for local or systemic infection.

Figure 2:
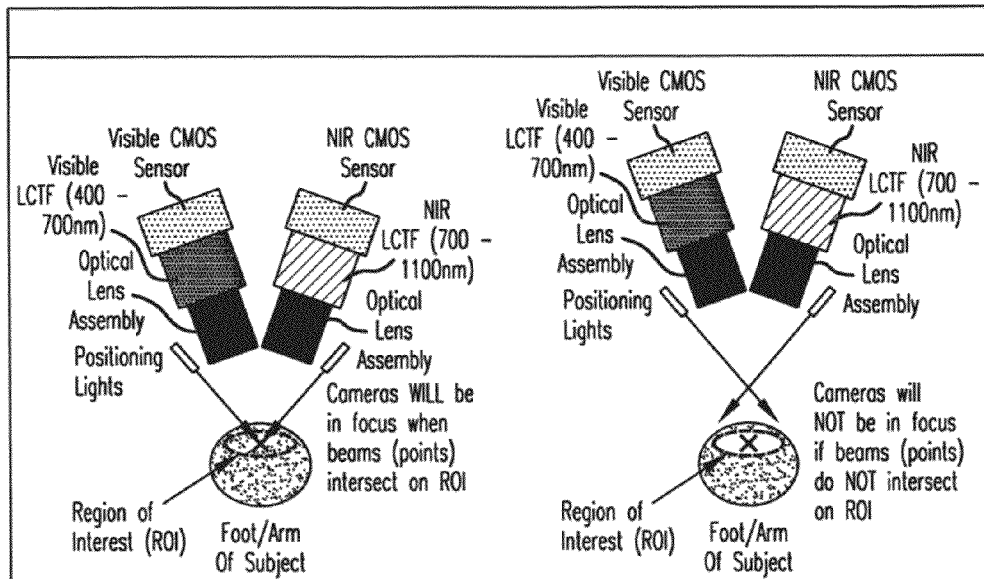
FIG. 2: Basic specifications of the MHSI system.

Yet another embodiment can give information about tissue hydration and potentially information about oxyHb and deoxyHb from deeper tissue using NIR wavelengths. These can be used as a stand alone device or as paired with the more standard Visible wavelength MHSI device as shown in FIG. 2.

Yet another embodiment can derive and present information from changes seen radiating from an area of wounded, ulcerated or otherwise abnormal tissue or from any change in tissue characteristics over a distance. A "gradient map" thus produced can be used to generate a diagnosis, predict the capability of the tissue to heal, define a level for amputation, define the infection vs inflammation, define areas of ischemia, define areas of tissue at risk for ulceration etc.

Another embodiment can involve dividing the region of interest into radial segments, pie like segments or a combination of the two or into squares or other geometric shapes and using these segments to compare and contrast different regions of tissue in the same field of view or as compared to a similar field of view on the contralateral extremity or on another part of the body (such as the forearm, the upper leg, etc.). The radial segments can also be compared to similar locations at different time points to demonstrate change over time in response to different therapeutic interventions, changes in tissue physiology, either local, regional or systemic due either to progression or remission of disease or of the effects of topical or systemic medications or therapies.

Such measurements can be used to evaluate wound healing, tissue regeneration, angiogenesis, vasculogenesis, arteriogenesis, infection, inflammation, microvascular disease or alterations, or other changes in tissue characteristics or physiology associated with the implementation of negative pressure (vacuum suction applied to the wound), hyperbaric therapy, grafting of autologuous, heterograft, xenograft or biological or synthetic skin substituetes, administration of topical agents including antibiotics, cleansers, growth factors, surgical intervention, angioplasty, stenting, atherectomy, laser therapy, vasodilator therapy, offloading, compression, effects of pressure due to orthotic or prosthetic, effects of electromagnetic, acupuncture, massage, infrared, vibration or other therapies.

Such measurements can be considered as biomarkers representing tissue oxygen delivery and oxygen extraction, tissue oxygenation, tissue perfusion, tissue metabolism or other characteristics correlated with MHSI measurements.

Such measurements can be used in association with the implementation of hyperbaric therapy delivered to assist in the healing of ulceration in diabetic or other foot ulceration, or other wounds in other parts of the body. In the case of hyperbaric oxygen therapy, the tissue can be monitored before and at specified intervals during therapy or continuously during therapy to determine when the tissue has been adequately modified (oxygenated) by the therapy or that there has been sufficient change in tissue metabolism as described by the MHSI measurements of oxyHb, deoxy Hb or other measured parameters or whether no benefit is being delivered. MHSI can be used to determine the appropriate duration of HBO therapy during a given session and as to whether sufficient benefit has been delivered from a course of therapy that it can safely be discontinued and that the wound will then be likely to heal with more standard methods.

MHSI can be used to determine the capability of tissue to heal after debridement and hence the relative safety of pursuing such an approach. Similarly, MHSI can be used to help determine the lowest level of amputation that can be performed with successful healing. Similarly MHSI can be used to determine whether elective surgery to the foot, lower extremity or other body part where evaluation and or quantitation of perfusion, oxygenation, or tissue metabolism would assist in determination of the safety of undertaking such a procedure or the location in which to direct such a procedure. MHSI can be utilized before debridement, amputation or other surgery to make this determination or during debridement, amputation\ or other surgery to better assess tissue to improve surgical outcomes.

Such measurements can be used for the determination of which patients or which wounds are likely to improve with any of the above mentioned therapies, which patients or wounds or portions of wounds are healing or worsening, when a given therapy is sufficient (this could be during or immediately after application of a therapy such as hyperbaric therapy or a debridement or a particular cleansing or pharmaceutical regimen or after a longer course of several days of therapy such as a vacuum therapy. MHSI criteria can be used to determine when a tissue will accept a skingraft or benefit from an allograft or other skin replacement.

Systemic or Regional Disease

One embodiment uses a single system that employs light wavelengths derived from the UV, visible, the near infrared, short wave infrared, mid infrared or far infrared portion of the electromagnetic spectrum. Another embodiment uses a system that uses one or more wavelengths from more than one of these wavelength regimes. One such system using wavelengths from more than one of these wavelength groupings is shown in figure two. In other embodiments, a single sensor could be used to collect light from more than one wavelength regime.

A portable hyperspectral imaging apparatus according to an embodiment of the invention is depicted in FIG. 1. Portable apparatus 10 weighs less than 100 pounds, preferably less than 25 pounds, and more preferably less than 10 pounds. Preferably, the portable apparatus may be battery operated, have some other form of portable power source or more preferably, may have a connector adapted to connect to an existing power source.

Portable apparatus 10 comprises an optical acquisition system 36 and a diagnostic processor 38. Optical acquisition system 36 comprises means to acquire broadband data, visible data, ultraviolet data, infrared data, hyperspectral data, or any combination thereof. In a preferred embodiment, optical acquiring means comprises a first-stage imaging optic 40, a spectral separator 42, a second-stage optic 44, and an imaging sensor 46. Alternatively, optical acquiring means may be any acquisition system suited for acquiring broadband data, visible data, ultraviolet data, infrared data, hyperspectral data, or any combination thereof. Preferably, one or more polarizers 41, 43 are included in the acquisition system to compile the light into a plane of polarization before entering the imaging sensor. Preferably, a calibrator is also included in the system.

If the spectral separator 42 does not internally polarizes the light, the first polarizer 43 is placed anywhere in the optical path, preferably in front of the receiving camera 46. The second polarizer 41 is placed in front of illuminating lights 20 such that the incident light polarization is controlled. The incident light is crossed polarized with the light recorded by the camera 46 to reduce specular reflection or polarization at different angles to vary intensity of the reflected light recorded by the camera.

The illumination is provided by the remote light(s) 20, various sources tailored or adapted to the need of the instrument, preferably positioned around the light receiving opening of the system, or otherwise placed to afford optimal performance. The light can be a circular array of focused LED lights that emit light at the particular wavelengths (or ranges) that are used in the processing algorithm, or in the ranges of wavelengths (e.g., visible and/or near-infrared). The circular arrangement of the light sources provides even illumination that reduces shadowing. The light wavelength selectivity reduces effect of the observation on the observing subject. The configuration may also vary depending on the particular needs and operation of the system.

Although the preferred embodiment describes the system as portable, a non-portable system may also be utilized. Preferably, an optical head is mounted to the wall of the examination room, more preferably, an overhead light structure is located in the operating room, or more preferably, the system has a portable table with an observational window overlooking the operating site.

The preferred embodiment may also be used as part of another instrument. For example, as an adjunct to an endoscope.

The first-stage optic receives light collected from a tissue sample through a polarizer and focuses the light onto the surface of the spectral separator. Preferably, the spectral separator is a liquid crystal tunable filter (LCTF). LCTF 42 is a programmable filter that sequentially provides light from selected wavelength bands with small (for example, 7-10 nm) bandwidth from the light collected from the sample. Second-stage optic 44 receives the narrow band of light passing through the spectral separator and focuses the light onto the image sensor 46. The image sensor is preferably, although not necessarily, a two-dimensional array sensor, such as a charge-coupled device array (CCD) or CMOS, which delivers an image signal to the diagnostic processor 38.

Diagnostic processor 38 includes an image acquisition interface 50, that has an input responsive to an output of the image sensor 46 and an output provided to a general-purpose operating module 54. The general-purpose operating module includes routines that perform image processing, and that operates and controls the various parts of the system. The general-purpose operating module also controls the light source(s) (e.g. LED array) allowing for switching on and off during measurement as required by the algorithm. The general-purpose operating module has control output provided to a filter control interface 52, which in turn has an output provided to the spectral separator 42. The general-purpose operating module also interacts with a number of diagnostic protocol modules 56A, 56B, . . . 54N, and has an output provided to a video display. The diagnostic process includes special purpose hardware, general-purpose hardware with special-purpose software, or a combination of the two. The diagnostic processor also includes an input device 58, which is operatively connected to the general-purpose operating module. A storage device 60 and printer 62 also are operatively connected to the general-purpose operating module.

In operation, a portable or semi-portable apparatus is employed within line of site (or with optical access) of the object or area of interest, e.g., diabetic foot with or without an ulcer, or general area of interest. An operator begins by selecting a diagnostic protocol module using the input device. Each diagnostic protocol module is adapted to detect particular tissue characteristics of the target. The diagnostic module could be specific for diabetes, for peripheral vascular disease, for venous stasis disease or for a combination of these disease states. As another example, a screening protocol for feet without ulcers or a potential for healing protocol for feet with ulcers. In an alternative embodiment, the apparatus may contain only one diagnostic module adapted for general medical diagnosis.

Diagnostic processor 38 responds to the operator's input by obtaining a series of transfer functions and an image processing protocol and an image processing protocol from the selected diagnostic protocol module 56. The diagnostic processor provides the filtering transfer functions to the spectral separator 42 via its filter control interface 52 and then instructs the image acquisition interface 50 to acquire and store the resulting filtered image from the image sensor 46. The general-purpose operating module 54 repeats these filtering and acquiring steps one or more times, depending on the number of filter transfer functions stored in the selected diagnostic protocol module. The filtering transfer functions can represent bandpass, multiple bandpass, or other filter characteristics and can include wavelengths in preferably the UV, preferably the visible, preferably the NIR and preferably, the IR electromagnetic spectrum.

In a preferred embodiment, the light source delivering light to the target of interest can be filtered as opposed to the returned light collected by the detector. Thus, a tunable source delivers the information. Alternatively, both a tunable source and a tunable detector may be utilized. Such tuning takes the form of LCTF, acousto-optical tunable filter (AOTF), filter wheels, matched filters, diffraction gratings or other spectral separators. The light source may be a tungsten halogen or xenon lamp, but is preferably a light emitting diode (LED).

The unique cool illumination provided by the LED prevents overheating of skin which may result in poor imaging resolution. Preferably, the LED provides sufficient light while producing minimal or no increase in skin temperature. This lighting system in combination with the polarizer allows adequate illumination while preventing surface glare from internal organs and overheating of skin. In certain embodiments, illumination can arise from more passive sources such as room lights or from sunlight.

Once the image acquisition interface 50 has stored images for all of the image planes specified by the diagnostic protocol chosen by the operator, the image acquisition interface begins processing these image planes based on the image processing protocol from the selected diagnostic protocol module 56N. Processing operations can include general image processing of combined images, such as comparing the relative amplitude of the collected light at different wavelengths, adding amplitudes of the collected light at different wavelengths, or computing other combinations of signals corresponding to the acquired planes. The computed image is displayed on the display 12. Other preferred embodiments include storing the computed image in the storage device 60 or printing the computed image out on printer 62.

In a preferred embodiment, a calibrator is included in the system. Calibrator has an area colored with a pattern of two (or more) colors. To optimize use of the calibrator for this particular application where oxyHb and deoxyHb are important components of the solution, colors are chosen that have a distinct absorption band in the wavelength range similar to oxyHb and deoxyHb—preferably in the range 500-600 nm. The colors are placed into a pattern, preferably, a checkerboard pattern, where 1 out of 4 squares has color1, and 3 out of 4 squares have color2. Thus, approximately 25% of the squares are color1 and 75% of the squares are color2. The system takes a hypercube being slightly out of focus—that provides blurring of colors into each pixel. From the spectra for each pixel, a linear composition of two spectra: one from color1 and another from color2 are observed. The recorded spectra are decomposed in a manner similar to a system that decomposes skin spectra into oxyHb & deoxyHb components. However, in this instance it takes pure color1 and color2 spectra from library instead of oxyHb & deoxyHb. Valid calibration reports concentrations of 75% for color2 and 25% for color1. Results are similar to skin analysis, where the output is approximately 90% of oxyHb and 10% of deoxyHb. Other embodiments include but are not limited to, changes to the pattern, the color concentration & intensity, and the number of colors.

In summary, the system simulates the way the biological mixture (oxyHb+deoxyHb) is observed by using "optical" mixture via combination of pattern (with known spatial concentrations) and analog blurring (defocusing—for speed. Defocusing can also be done in the software through the use of computational filters).

If the correct result is obtained, confirmation of the lighting distribution and collection throughput, and the wavelength accuracy of the system given confidence in the spectra (wavelengths and intensity) that are being collected are provided. This provides additional assurance that the data recorded off the patient is acceptable.

In another preferred embodiment, diagnostic protocol modules 56, printer 62, display 12, or any combination thereof, may be omitted from portable device 10. In this embodiment, acquired images are stored in storage device 60 during the medical procedure. At a later time, these images are transferred via a communications link to a second device or computer located at a remote location, for example, hospital medical records, for backup or reviewing at a later time. This second device can have the omitted diagnostic protocol modules, printer, display, or any combination thereof. In another embodiment, the stored images are transferred from portable device 10, located in the clinic, via a communications link to a remote second device in real time.

In a preferred embodiment the system has facility to project real-time hyperspectral data onto the operation field, region of interest, or viewing window positioned above the operating site. Heads Up Display. Also, display completely separately for remote guidance (i.e. on a wall screen for a group of people to review in real time, or post procedure). The projected information has precise one-to-one mapping to the illuminated surface (e.g. wound, operating surface, tissue) and provides the surgeon or podiatrist with necessary information in efficient and non-distractive way. When projected onto an overhang viewing window, the images (real-color and/or pseudo-color) can be zoomed in/out to provide variable magnification. This subsystem consists of the following elements: 1) image projector with field-of-view precisely co-aligned with the field-of-view of the hyperspectral imager, 2) miniature remote control device which allows the surgeon or podiatrist to switch projected image on and off without turning from the site of debridement and change highlight structure and/or translucency on the projected image to improve visibility of the features of interest as well as projected image brightness and intensity, 3) real-time data processing package which constructs projected image based on hyperspectral data and operator/surgeon input, 4) optional viewing window positioned above the operating site that is translucent for real observation or opaque for projecting pseudo-color solution or higher resolution images.

The MHSI system consists of three functional modules—a Spectral Imager (SI), supporting Controller and Power Module (CPM) and Control and Data Acquisition Computer (CDAC). The MHSI also includes a thermometer that remotely measures the temperature at the tissue surface. The Spectral Imager is mounted on suspension arm which neutralizes device weight and allows for easy positioning and focusing of the instrument. The suspension arm is attached to wheeled cart which supports CPM and CDAC as well. This configuration is very mobile and permits wide range of device spatial and directional motions.

FIG. 2 shows the preferred system specifications along with a diagram of our focusing methodology and the optical design of the Spectral Imager. In this embodiment, a liquid crystal tunable filters (LCTF's) was used as the wavelength selector and are coupled to complementary metal oxide semiconductor (CMOS) imaging sensors. Fitted with macro lenses and the positional light focusing system described below, the system has a preferred working focal length of roughly 1 to 2 feet.

A major issue in the collection of hyperspectral imaging data is the position and focusing of the instrument. While our Spectral Imaging Module is positioned on a ball joint that allows free rotation and virtually any angle of incidence to the patient, it is imperative that there be a system in place for targeting the image to a particular spot on the tissue and ensuring that the instrument will be at the proper distance from the tissue to achieve optimal focus. Positioning and focusing with our system are facilitated by two mirrored collimated light beams or lasers that cross precisely at the instrument focal plane (FIG. 2), and so bringing the spectral imaging module into position where the two light spots overlap on the tissue to insure optimal focus.

To achieve precisely calibrated images, the system may use a specially designed calibration pad placed at the focal plane of the system and measured prior to each patient measurement. The calibration pad includes a diffusely reflective surface to quantify the intensity of the illumination at each wavelength and color bars to validate wavelength accuracy of the system. Calibration data measured at a preset time such as during maintenance calibrations can be stored and compared to with each use to decide whether the system is within specifications and should proceed to patient measurements.

To achieve precise co-registration between hyperspectral image and operating surface, the system may use a fiducial label or target placed in the field of view which the image registration module can perform a self-alignment procedure before or during the operation as necessary.

Devices of the present invention allow for the creation and unique identification of patterns in data that highlight the information of interest. The data sets in this case may be discrete images, each tightly bounded in spectra that can then be analyzed. This is analogous to looking at a scene through various colored lenses, each filtering out all but a particular color, and then a recombining of these images into something new. Such techniques as false color analysis (assigning new colors to an image that don't represent the true color but are an artifact designed to improve the image analysis by a human) are also applicable. Optionally, optics can be modified to provide a zoom function, or to transition from a micro environment to a macro environment and a macro environment to a micro environment. Further, commercially available features can be added to provide real-time or near real-time functioning. Data analysis can be enhanced by triangulation with two or more optical acquisition systems. Polarization may be used as desired to enhance signatures for various targets.

In addition to having the ability to gather data, the present invention also encompasses the ability to combine the data in various manners including vision fusion, summation, subtraction and other, more complex processes whereby certain unique signatures for information of interest can be defined so that background data and imagery can be removed, thereby highlighting features or information of interest. This can also be combined with automated ways of noting or highlighting items, areas or information of interest in the display of the information.

The hyperspectrally resolved image in the present invention is comprised of a plurality of spectral bands. Each spectral band is adjacent to another forming a continuous set.

Preferably, each spectral band having a bandwidth of less than 50 nm, more preferably less than 30 nm, more preferably less than 20 nm, more preferably, from about 20-40 nm, more preferably, from about 20-30 nm, more preferably, from about 10-20 nm, more preferably from about 10-15 nm, and more preferably from about 5-12 rim.

It is clear to one skilled in the art that there are many uses for a medical hyperspectral imager (MHSI) according to the invention. The MHSI offers the advantages of performing the functions for such uses faster, more economically, and with less equipment and infrastructure/logistics tail than other conventional techniques. Many similar examples can be ascertained by one of ordinary skill in the art from this disclosure for circumstances where medical personal relies on their visual analysis of the biological system. The MHSI acts like "magic glasses" to help human to see inside and beyond.

Algorithm Description

The embodiment of diabetes algorithm involves the following steps:

1 Preprocess the MHSI data. Preferably, by removing background radiation by subtracting the calibrated background radiation from each newly acquired image while accounting for uneven light distribution by dividing each image by the reflectance calibrator image and registering images across a hyperspectral cube.
2. Build a color-photo-quality visual image. Preferably, by concatenating three planes from the hyperspectral cube at the wavelengths that approximately correspond to red (preferably in the range of about 580-800 nm, more preferably in the range of about 600-700 nm, more preferably in the range of about 625-675 nm and more preferably at about 650 nm), green (preferably in the range of about 480-580 nm, more preferably in the range of about 500-550 nm, more preferably in the range of about 505-515 nm, and more preferably at about 510 nm), and blue (preferably in the range of about 350-490 nm, more preferably in the range of about 400-480 nm, more preferably in the range of about 450-475 nm, and more preferably at about 470 nm) color along the third dimension to be scaled for RGB image.
3. Define a region of interest (ROI), preferably, where the solution is to be calculated unless the entire field of view to be analyzed.
4. Convert all hyperspectral image intensities into units of optical density. Preferably, by taking the negative logarithm of the decimal base. FIG. 2 shows examples of spectra taking from single pixels at different tissue sites within an image. Tissue sites include connective tissues, oxygenated tissues, muscle, tumor, and blood.
5. Decompose the spectra for each pixel (or ROI averaged across several pixels). Preferably, decompose into several independent components, more preferably, two of which are oxyhemoglobin and deoxyhemoglobin.
6. Determine three planes for pseudo-color image. Preferably, define the color hue plane as apparent concentration of oxygenated Hb, or deoxygenated Hb, or their mathematical combination, e.g. total Hb, oxygen saturation, etc. Preferably, define the color saturation plane as apparent concentration of oxygenated Hb, or deoxygenated Hb, or their mathematical combination, e.g. total Hb, oxygen saturation, etc. Preferably, define the color intensity (value) plane as reflectance in blue-green-orange region (preferably in the range of light at about 450-580 nm).
7. Adjust the color resolution of the pseudo-color image according to quality of apparent concentration of oxygenated Hb, or deoxygenated Hb, or their mathematical combination, e.g. total Hb, oxygen saturation, etc. Preferably, reduce resolution of hue and saturation color planes by binning the image (e.g. by 2, 3, 4, etc. pixels), or/and by resizing the image, or/and by smoothing the image through filtering higher frequency components out. Interpolate the smoothed color planes on the grid of higher resolution intensity (value) plane.
8. Convert hue-saturation-value/intensity (HSV/I) image to red-green-blue (RGB) image.
9. Remove outliers in the resulting image, defining an outlier as color intensity deviating from a typical range beyond certain number of standard deviations, preferably three. Stretch the resulting image to fill entire color intensity range, e.g. between 0 and 1 for a double precision image.
10. Display ROI in pseudo-colors, preferably, in combination with the color photo image of the subject, or preferably, in addition to the color photo image of the subject, or more preferably, by projecting the pseudo-color image onto the observed surface. Additional information can be conveyed through images portraying the individual coefficients from oxyHb, deoxyHb, slope and offset coefficients, or any linear or nonlinear combination such as the oxyhemoglobin to deoxyhemoglobin ratio.
11. Characterize the metabolic state of the tissue of interest (e.g. risk for ulceration, potential to heal). Preferably, by using the saturation and/or intensity of the assigned color and provide a qualitative color scale bar.

As is clear to a person of ordinary skill in the art, one or more of the above steps in the algorithm can be performed in a different order or eliminated entirely and still produce adequate and desired results. Preferably, the set of instructions includes only the steps of preprocessing the hyperspectral information, building a visual image, using the entire field of view, converting all hyperspectral image intensities into units of optical density by taking a negative logarithm of each decimal base, and characterizing a metabolic state of the tissue of interest. More preferably, the set of instructions comprises preprocessing the hyperspectral information, defining a region of interest of the tissue, and characterizing a state of the tissue of interest.

Another preferred embodiment entails reducing the hyperspectral data in the spectral dimension into a small set of physiologic parameters involves resolving the spectral images into several linearly independent images (e.g. oxyhemoglobin, deoxyhemoglobin, an offset coefficient encompassing multiple scattering (MS) properties and a slope coefficient) in the visible regime. Another embodiment determines four images (e.g. oxyhemoglobin, deoxyhemoglobin, offset/scattering coefficient, and water absorption) in the near infrared region of the spectrum. As an example for the visible region of the spectrum, linear regression fit coefficients c1, c2, c3 and c4 will be calculated for reference oxy-Hb, deoxy-Hb, and MS spectra, respectively, for each spectrum ($S_{ij}$) in an image cube:

$$\vec{S_{ij}} = \|c_1 \vec{OxyHB} + c_2 \vec{DeoxyHB} +$$

-continued $$\overrightarrow{c_3 \text{Offset} + c_4 \text{Slope}}\|_2$$

Individual images of the oxyhemoglobin and deoxyhemoglobin components, the slope and offset or any combination, linear or nonlinear, of these terms, for example the oxy- to deoxyhemoglobin ratio, can be presented in addition to producing the pseudo-colored image to the user.

Figure 3:
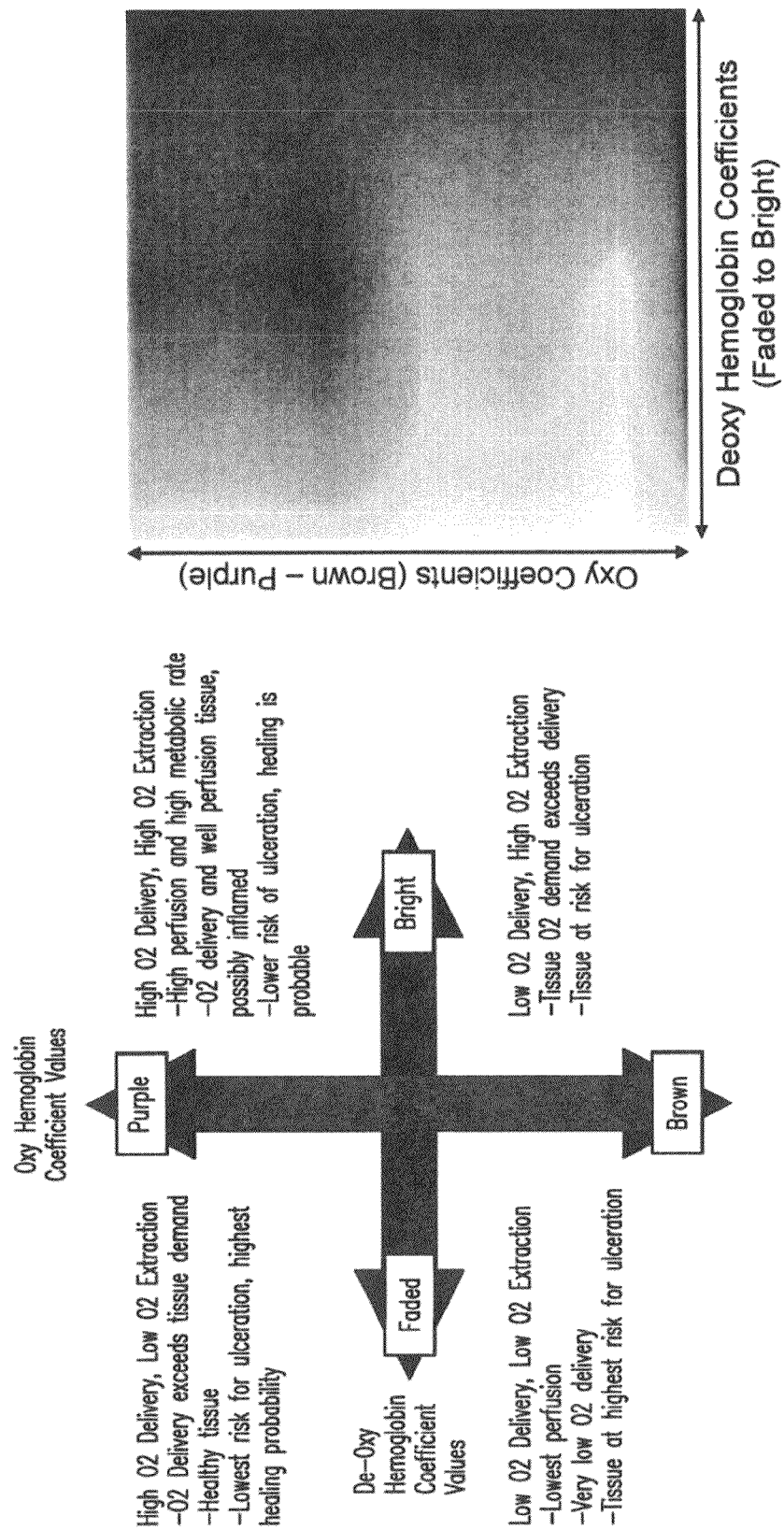
FIG. 3: OxyHb and DeoxyHb HSV/I color chart. Schematic representation of the MHSI display (left) showing the interplay between the oxyHb and deoxyHb coefficients and describing some of the potential physiological consequences of values of the MHSI.

In order to present the MHSI effectively, a display method was developed that has the potential to convey a 2-dimensional index, and convey the values for both the oxy and deoxyhemoglobin coefficients independently. The method of displaying our index uses a color scale, in one iteration this ranges from purple values (high) to brown values (low) to indicate the concentration of oxyhemoglobin in the tissue, and a brightness scale, ranging from very bright (high) to faded (low) associated with the tissue concentration of deoxyhemoglobin. FIG. 3 summarizes the display of the MHSI, showing a schematic diagram explaining the scenarios of low and high oxy and deoxy hemoglobin coefficients as well as a color scale that indicates a color plat that shows the vertical color scale and the horizontal brightness scale. By measuring an MHSI where the oxyhemoglobin component is high and the deoxyhemoglobin component is low (upper left hand corner of FIG. 3), it could be concluded that that particular area of tissue has adequate perfusion and oxygenation, and is able to satisfy its metabolic needs with the oxygen that is being delivered. That this tissue has the lowest level of risk for ulceration and the highest probability of healing. If tissue demonstrates a low oxyhemoglobin level in addition to a low deoxyhemoglobin level (lower left corner of FIG. 3), this would imply that the tissue was receiving low total volume of blood. If tissue demonstrates a low oxyhemoglobin level in addition to a high deoxyhemoglobin level (lower right corner of FIG. 3) this would imply that the tissue has metabolic requirements exceeding available oxygen delivery. In both of these regions there is expected to be a higher risk of ulceration or difficulties with wound healing. If the tissue has a high oxyhemoglobin coefficient and also has a high deoxyhemoglobin content, (lower left corner of FIG. 3) this tissue was receiving a larger total volume of blood, and that the oxygen extracted from the blood stream was adequate to support tissue metabolism. This could be indicative of inflammation. Our technique will uniquely permit discrimination between each of these disparate physiologic conditions. For example, if the value is faded purple (upper left hand quadrant) the tissue has very high oxygenation, as discussed above, and is very likely to heal. The color map (right) gives an indication of how the MHSI would be represented in an image format.

Describe here is hyperspectral imaging for use in the peripheral vascular and diabetes clinic, designed both to be mobile for ease of use and to facilitate the most accurate data collection possible for this project. This system provides fast and precise measurement of reflectance spectra, and is characterized by high spatial and spectral resolution, the ability to process spectral data in real time. It has been equipped with a turn-key software interface for the user. Proprietary image registration software insures image stability when measuring spectra of animated objects. The system does not rely on external illumination, rather it contains very efficient internal visible (and NIR in certain versions) light sources, which allow to achieve high signal to noise ratios in measured data without putting noticeable heat load on a biological subject (variations in skin temperature during acquisition are on the order of 0.1 C).

Figure 4:
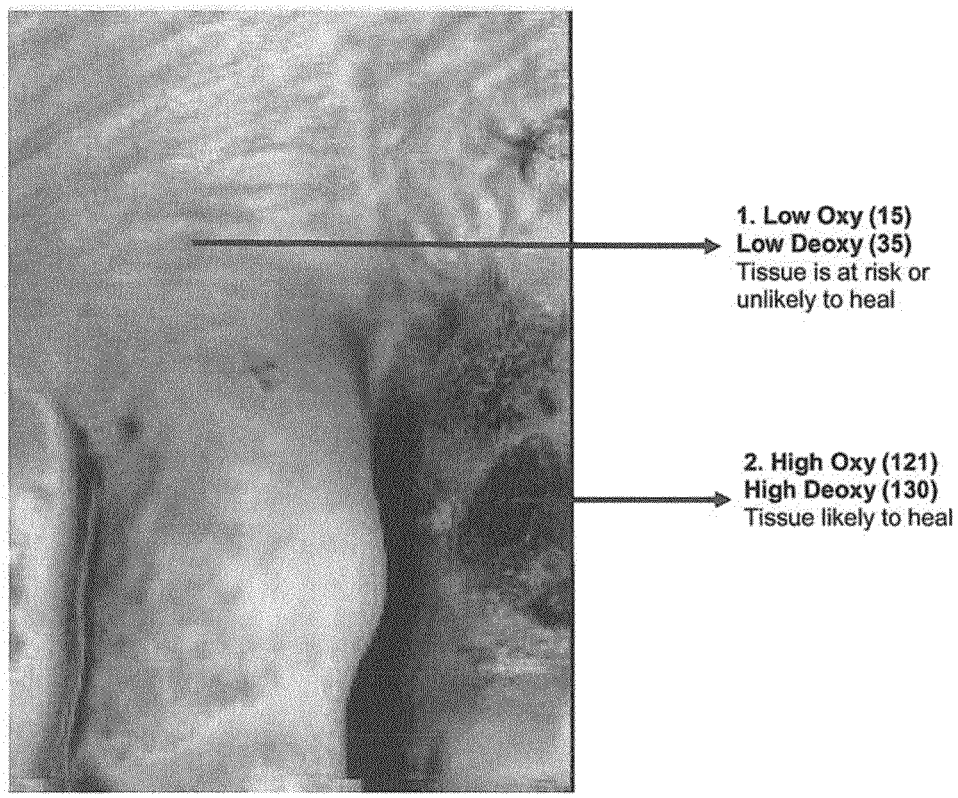
FIG. 4: Representative data from dorsal surface of foot showing individual oxyHb and deoxyHb values and how they can be used to evaluate regions of the tissue.

All MHSI data were corrected for background and uneven illumination, and normalized by the integration time. The data were ratioed to the reflectance of a calibration standard, and negative decimal logarithm was taken to obtain the absorption data. Images at all wavelengths were co-registered using proprietary software developed by HyperMed to ensure that each pixel represents the same point on the skin throughout all wavelengths. The spectra were then deconvolved into four linearly-independent spectral components with coefficients representing the amount of hemoglobin (both oxyHb and deoxyHb) in the observed skin. Typically two numbers are presented x/y wherein x represents oxyHb and y is deoxyHb. The values for x and y can be taken from a single pixel or from a ROI defined by the user. In addition the hemoglobin oxygen saturation ($S_{HSI}O_2$), x/(x+y), can be presented for a pixel or a ROI. FIG. 4 shows examples of tissue with low and high oxyHb and deoxyHb values corresponding to tissue at risk of ulceration and a wound that is likely to heal, respectively. Another way of presenting linearly independent variables is through their sum and difference: (x+y) and (x−y). The first would be THb, and the second would "hint" on oxygen extraction—which indicates the kind of Hb that is predominant at the site.

Data in the following table represent typical oxyHb, deoxyHb, and $S_{HSI}O_2$ values for two body positions, forearm and foot, and for various stages of diabetes: nondiabetics, diabetics without peripheral neuropathy, and diabetics with peripheral neuropathy. In general, the value for oxyHb and $S_{HSI}O_2$ are lower in the feet of diabetic subjects with neuropathy compared to the other two groups, a group at high risk for developing foot ulcers. In addition, the values for oxyHb, deoxyHb, and $S_{HSI}O_2$ depend on body location, that once calibrated can be accounted for by the diagnostic module.

MHSI oximetry values at baseline (prior to iontophoresis of acetylcholine)

| Site | Group (N) | Oxy | Deoxy | $S_{HSI}O_2$ (%) |
|---|---|---|---|---|
| Forearm | Control (21) | 29 ± 7* | 41 ± 16 | 42 ± 17** |
| | Diabetic Non-Neuropathic (36) | 20 ± 5 | 44 ± 10 | 32 ± 8** |
| | Diabetic Neuropathic (51) | 19 ± 7 | 49 ± 10 | 28 ± 8** |
| Dorsum of foot | Control (21) | 25 ± 13 | 44 ± 18 | 38 ± 22 |
| | Diabetic Non-Neuropathic (36) | 24 ± 9 | 41 ± 11 | 37 ± 12 |
| | Diabetic Neuropathic (51) | 19 ± 9*** | 45 ± 13 | 30 ± 12**** |

*p < 0.0001 compared to diabetics with and without neuropathy
**p < 0.0001 for all three groups
***p < 0.025 when compared to control and nonneoropathic
****p < 0.027 when compared to control and nonneoropathic In summarizing these data, MHSI provides relevant physiological information at the systemic, regional and local levels. Forearm data measures systemic microvasculature changes since the forearm is not affected by macrovasculature or somatic neuropathy as found in the lower extremities. Dorsal foot measurements are indicative of microvascular and macrovascular effects including atherosclerotic changes occurring in large vessels exacerbated by diabetes. MHSI data from the right and left lower extremity can be compared to help differentiate the stages of the damage. Finally, MHSI can be used to find local information that can be associated to the risk of developing a foot ulcer of the progression of disease by examining the area around an ulcer.

MHSI can not only be used for determining risk of foot ulceration, but also for determining systemic progression of diabetic microvascular disease. In one embodiment this is determined by mean oxyHb, deoxyHb and/or other values for a region of interest. In another embodiment this is determined by heterogeneity of oxyHb, deoxyHb and/or other values for a region of interest. In another embodiment this is determined by the patterning of oxyHb, deoxyHb and/or other values for a region of interest. In other embodiments this is determined by changes over a given time period within a measurement session (between 1 picosecond and one hour, preferably between 100 microseconds and 10 minutes and more preferably between 100 microseconds and 15 seconds) and in the mean values or patterns of oxyHb, deoxyHb and/or other values for a region of interest. These measurements can be used to determine a diabetes progression index (DPI). Alternatively, a DPI can be calculated by comparing a MHSI value or set of values from a single point in time with another point in time (preferably 1 month to two years, more preferably 2 months to one year and most preferably 3-6 months)

Figure 5:
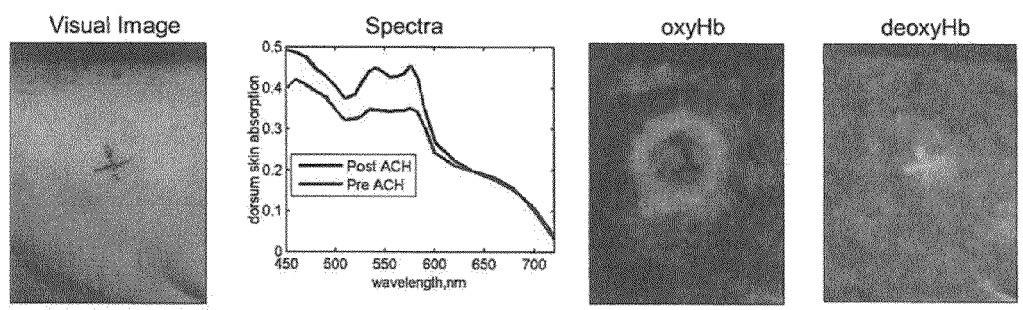
FIG. 5: Representative data from tissue showing sensitivity of MHSI to drug-induced changes in the vasculature. (left to right) Visible image of foot surface post iontophoresis (IP), representative spectra pre and post iontophoresis with Acetylcholine (IP) showing greater oxyHb levels after IP. Images of increased oxyHb coefficient ring where IP occurred, image of deoxyHb, showing little change post IP.

Using the active stimulus of acetylcholine as a vasodilator, and the known effects of this on LD measurements data was derived in which changes in MHSI could be observed under known alterations in physiology and compare these with baseline images and with LD data (FIG. 5). Using data collected from diabetic patients, as well as previous data from human shock studies and iontophoresis studies, an algorithm was derived that clearly discriminates regions vasodilated by iontophoresis and also discriminates ulcer from non ulcer with a proprietary formula that includes terms for oxyHb and deoxyHb. This was further developed as a Hyperspectral Microvascular Index (HMI), which is a metric of tissue physiology and have explored the use of the MHSI in evaluating tissue of the foot. In circumstances when an ulcer has been present, tissue was examined within the ulcer, directly adjacent to the ulcer, surrounding the ulcer and at various other regions of the foot.

With the aid of MHSI, a quantitative metric is demonstrated with superb separation between ulcerated or wounded and non-ulcerated or wounded tissue. Areas of different tissue metabolism can be seen with 60 micron (20-120) spatial resolution. Regions with an increased MHSI associated with the margins of the ulcer can be seen which correlate to inflammation (and/or infection). Areas of decreased MHSI can be seen in other areas which from previous work in ischemia is considered to be tissue at risk for non-healing, ulcer extension, or primary ulceration. These data validate the capability of our measurement system to have the resolution and appropriate range to quantitatively assess different areas of tissue metabolism on both dorsal and plantar foot surfaces as well as skin on other body areas or other tissues visible through endoscopic techniques or at the time of open surgery of the foot, leg, arm or any other body part including internal organs at laparoscopy or the retina at retinoscopy. The invention provides the capability to perform this quantitative assessment on tissue that demonstrates no visible differences on clinical examination to the skilled examiner.

Figure 6:
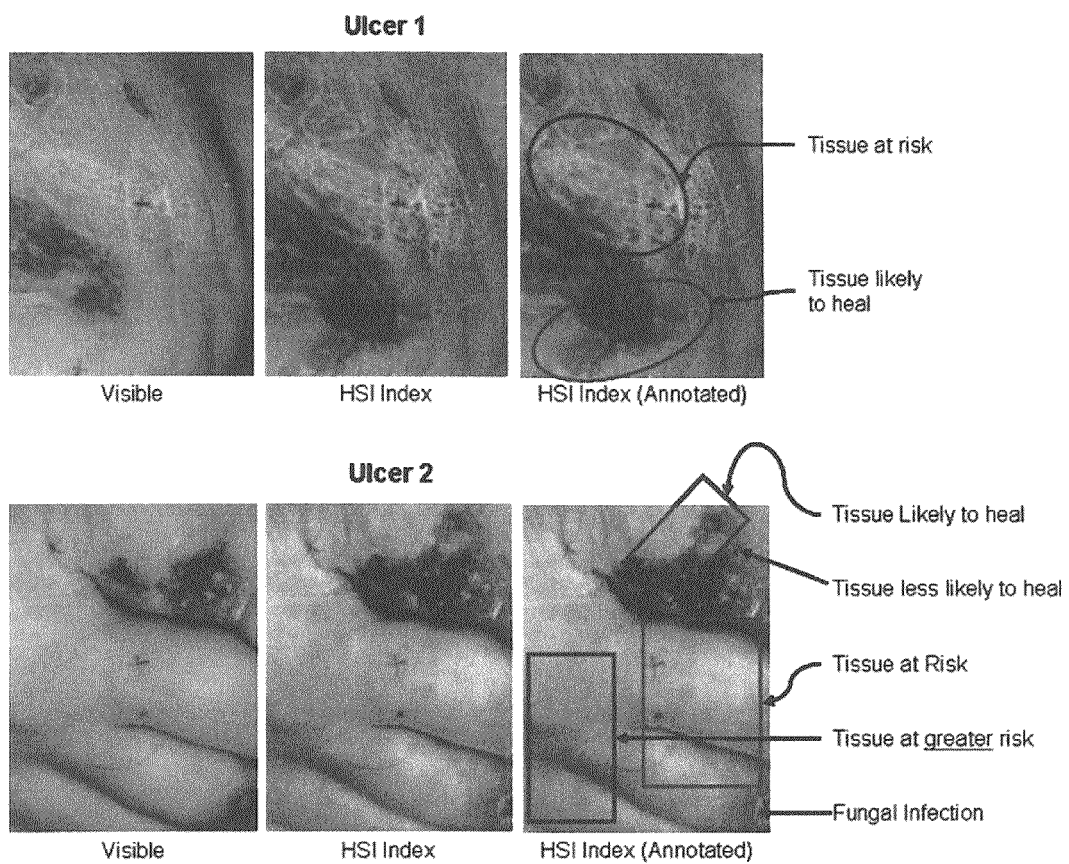
FIG. 6: Representative data from an ulcer located on the sole (ulcer 1) and dorsal surface (ulcer 2) of the foot.

MSHI images have the ability to differentiate between regions of tissue associated with a present foot ulcer on the basis of biomarkers such as the oxyHb and deoxyHb coefficients. FIG. 6 shows an ulcer on the sole of the foot of a type 1 diabetic patient (ulcer 1). From the visible image on the left, little distinguishes one area of the ulcer from another. However when looking at the image with the MHSI, there is obvious discriminatory power between the state of tissue seen in the purple oval, which is likely to heal, and that surrounded by the black oval, which is tissue at risk for further ulceration. It is important to note that the skin on the sole of this patient's feet is highly calloused, with a thick stratum corneum, but one is still able to differentiate tissue based on its spectral signatures. Given that the sole of the foot is often the site of the thickest stratum corneum on the body, the device works on all naturally or surgically exposed tissue or tissue otherwise visualized with laparoscopy, endoscopy, retinoscopy or other visualization techniques. Ulcer 2 was located on the dorsal surface of the foot, on the patient's big toe (FIG. 6). These images further show the ability to differentiate between tissue at risk and tissue likely to heal. Additionally, tissue surrounding a fungal infection on the patient's middle toe (bottom right-hand corner of the image) has an MHSI that can demonstrate inflamed or infected tissue.

Figure 7:
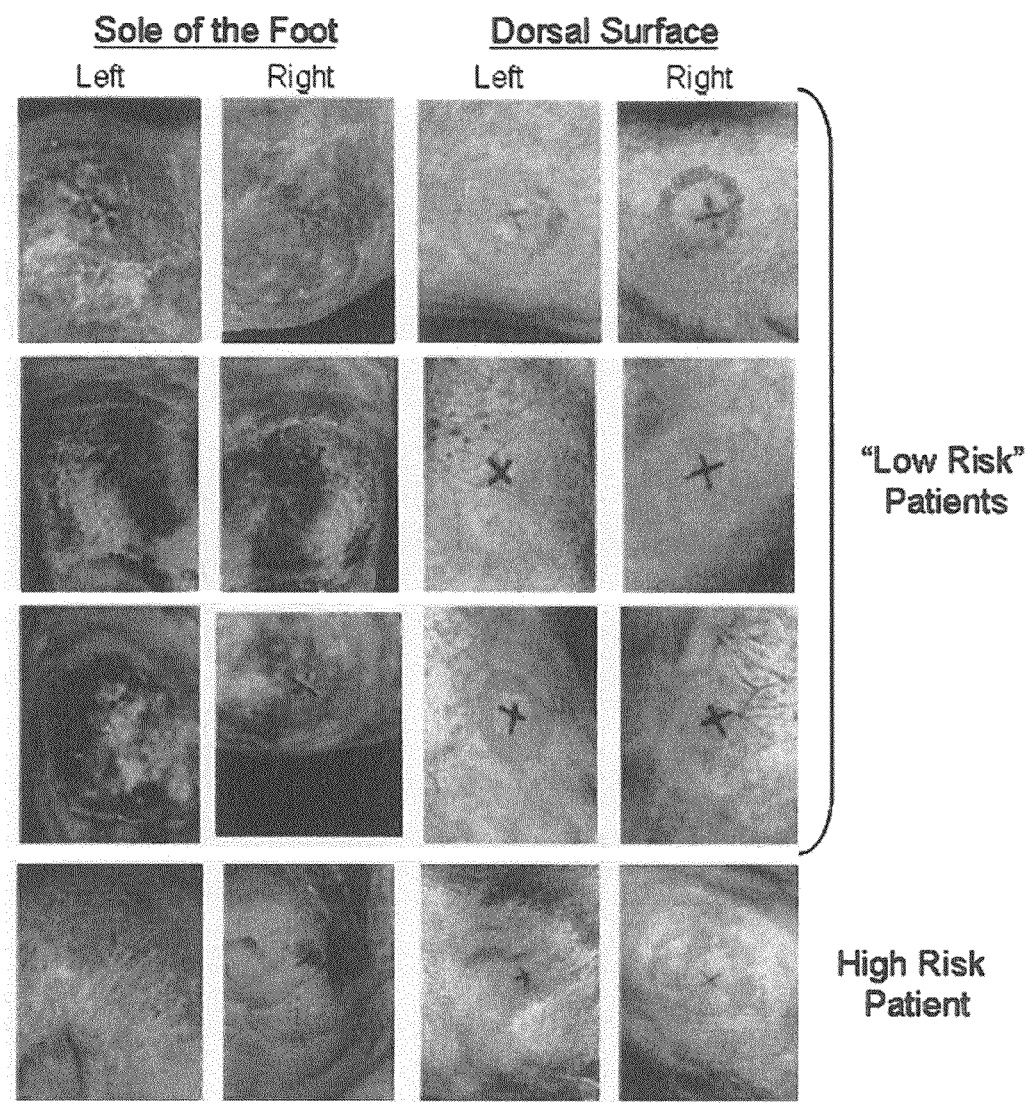
FIG. 7: MHSI information from the soles and dorsal surfaces of four patients. Each row of images represents data from one patient. The two columns on the left represent data from the soles of the feet, while the columns on the right represent data from the dorsal surfaces of the feet.

In addition to the differentiation of local tissue, tissue can be examined for gross features indicative of global risks of complications, such as poor perfusion or the inability of the microcirculation to react and compensate in tissue. In another embodiment, iontophoretic application of the vasodilator acetylcholine (ACH) or nitroprusside was used to stimulate the vasodilation of the microvasculature on the dorsal surface of the foot and on the forearm of the patients and measured the reaction with MHSI (FIG. 7).

The potential of hyperspectral imaging in diagnosing global microcirculatory insufficiencies and impacting on other complications of diabetes associated with the microvasculature besides foot ulcers. In FIG. 7, hyperspectral measurements from the feet of four patients, with the first two columns of images showing the MHSI of the soles of both feet, and the second two columns showing images of the dorsal surfaces of both feet after the application of ACH via iontophoresis. In the first three patients, an MHSI is seen that is much healthier than that of the fourth patient. Consequently, the fourth patient had a foot ulcer at the time of this study and has a previous history of ulceration. While the contrast between the data from the soles in these patients is striking, there is complementary information in the data from the microvascular response shown in the two columns on the right. Note that the first three patients all have MHSI scores that contain purple information in response to vasodilation, while the fourth patient shows what would be considered an MHSI that was indicative of tissue that was at risk. Microcirculatory changes associated with the progression of diabetes can also be modified by different treatment and therapeutic regimens and with the overlay of other systemic diseases (such as congestive heart failure or hypertension) or treatments or therapies for systemic diseases.

Figure 8:
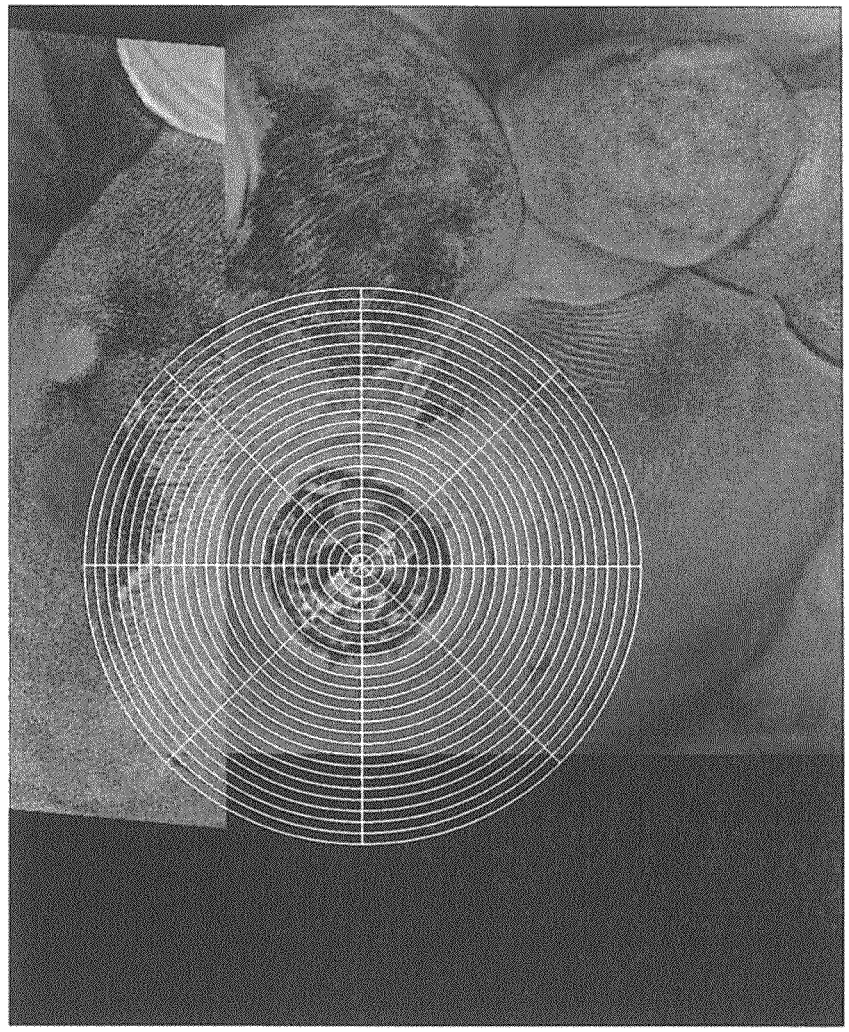
FIG. 8: MHSI image of diabetic foot ulcer with 200 segment radial profile.

To analyze the ulcer data further, ulcer images were divided into 25 concentric circles 1 mm apart and 8 pie segments forming 200 sectors per ulcer (FIG. 8). A radial profile analysis was undertaken where the ulcer center was defined at the first visit, and registered images from subsequent visits to this. OxyHb, deoxyHb, total-hemoglobin and $O_2$Sat were calculated for each sector.

Each radial pie segment was evaluated for signs of healing, nonhealing or progression in subsequent visits. MHSI measurements and clinical healing results were compared. MHSI algorithms were developed to identify changes associated with ulcer healing, nonhealing and progression. A primary endpoint evaluated the specific sectors of tissue around an ulcer that would heal, not heal or progress. The group estimates for oxyHb, deoxyHb, and $O_2$Sat are given in the following table using a linear mixed effects regression model. Significant differences were seen for healing for the oxyHb and deoxyHb values. Patients who did not heal also demonstrated increased heterogeneity in distant foot and in arm measurements. For the 21 ulcers studied, the algorithm predicted 6 of 7 ulcers that did not heal and 10 of 14 ulcers that healed.

Conclusion: MHSI identifies microvascular abnormalities in the diabetic foot and provides early information assist in managing foot ulceration and predict outcomes in patients with diabetes.

| MHSI | Group Estimates (±SEM) | | p-value |
|---|---|---|---|
| | Not Healing | Healing | |
| OxyHb | 36.4 + 2.2 | 51.9 ± 1.8 | <.0001 |
| Deoxylib | 34.2 ± 1.9 | 47.8 ± 1.6 | <.0001 |
| $S_{HSI}O_2$ | 0.51 ± 0.01 | 0.51 ± 0.01 | 0.8646 |

Figure 9:
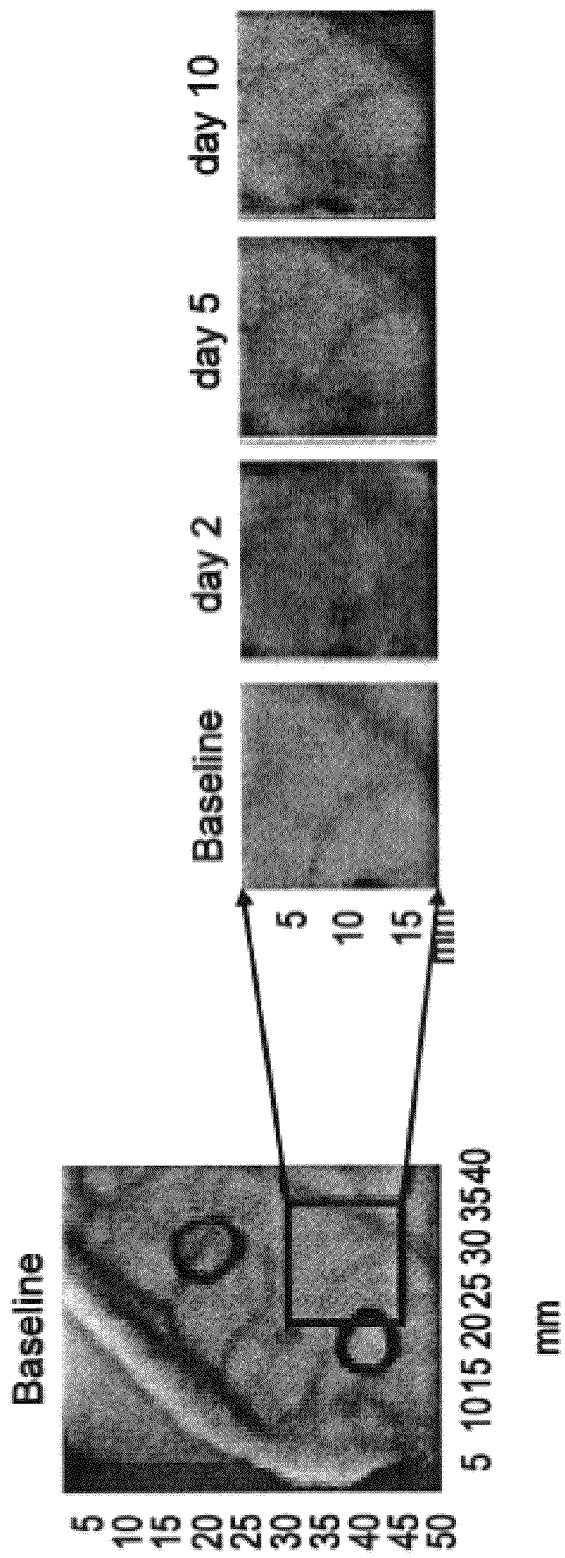
FIG. 9: MHSI of wounds during healing. The 50-micron resolution images of a rabbit's ear taken with MHSI (Medical Hyperspectral Imaging) system (HyperMed, Inc.) over 10 days period. Reconstructed from MHSI data, shows a part of the observed area 50-by-40 mm, recorded at the baseline on day 1. The black rings denote location of a future wound—puncture.

MHSI is used to monitor angiogenesis during wound healing. An example of wound healing in a diabetic rabbit wound model shows that during the healing process, images of oxyHb and deoxyHb show patterns that change in shape, area, and amplitude with time. Similar patterns were noted in experimental models of shock, but the changes observed for shock occurred on a shorter time scale; minutes rather than several days as the wound heals. The rabbit's ears were observed at days 1, 2, 5, and 10. MHSI is ideally suited for characterization of the local heterogeneity in oxyHb and deoxyHb and their spatial changes with time. For example, the zone of hyperemia surrounding a wound as measured by the oxyHb coefficient decreases with time in wounds that heal (FIG. 9). The color image (a), reconstructed from MHSI data, shows a part of the observed area 50-by-40 mm, recorded at the baseline on day 1. The black rings denote location of a future wound. The pseudocolor image (b), obtained as a result of hyperspectral processing, shows distribution of the oxyHb and deoxyHb in the underlying tissue at the same time. The color hue represents apparent oxyHb concentrations, whereas color saturation (from fade to bright) represents apparent deoxyHb concentrations. Both, oxyHb and deoxyHb vary predominantly between 40 and 90 MHSI units (color bar to the right). The remaining images to the right show change in a region of interest 17-by-17 mm (black box in (a) and (b)) over 10 days. At day 2, the oxy concentrations increased significantly in the area as far as 10 mm away from the wound border. By day 5, the increase in oxygenation became more local (purple area, shrunken to about 5 mm) and new microvasculature formed to feed the area in need (red fork-like vessels in the right top corners appearing in days 5 and 10 images). By the 10th day, the area of increased oxyHb has not changed much, but the peak in oxy amplitude decreased, suggesting a period of steady healing.

Figure 10:
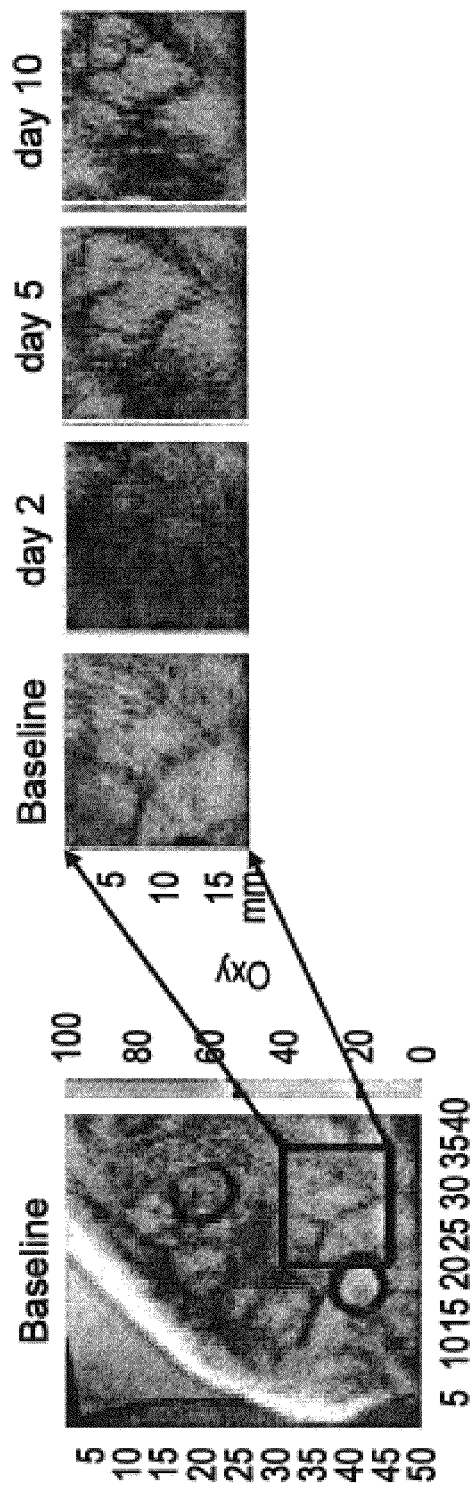
FIG. 10: Obtained as a result of hyperspectral processing, shows distribution of the oxygenated (oxy) and deoxygenated (deoxy) hemoglobin in the underlying tissue at the same time. The color hue represents apparent oxy concentrations, whereas color saturation (from fade to bright) represents apparent deoxy concentrations. Both, oxy and deoxy, vary predominantly between 40 and 90 mhsi units (colorbar to the right). The series of images to the right show change in a region of interest 17-by-17 mm (black box in a) and b)) over 10 days following the puncture wound initiated at day 1. At day 2, the oxy concentrations increased significantly in the area as far as 10 mm away from the wound border. By day 5, the increase in oxygenation became more local (purple area "shrunken" to about 5 mm) and new microvasculature formed to "feed" the area in need (red fork-like vessels in the right top corners appearing in the images for days 5 and 10). By the 10th day, the area of increased oxy has not changed much, but the peak in oxy amplitude decreased, suggesting a period of steady healing.

As depicted in FIG. 10, 50-micron resolution images of a rabbit's ear were taken with MHSI over a ten day period. In FIG. 10(a), the color image was reconstructed from MHSI data, showing a party of the observed area 50-by-40 mm, recorded at the baseline on day 1. The pseudo-image (b) was obtained as a result of hyperspectral processing, showing a distribution of the oxygenated (oxy) and deoxygenated (deoxy) hemoglobin in the underlying tissue at the same time.

Other embodiments and uses of the invention will be apparent to those skilled in the art from consideration of the specification and practice of the invention disclosed herein. All references cited herein, including all publications, U.S. and foreign patents, and patent and provisional applications, and all publications and documents cited herein for any reason, are specifically and entirely incorporated by reference. It is intended that the specification and examples be considered exemplary only.

LITERATURE CITED

1. International Diabetes Federation. Information on Global Diabetes Prevalence. In: http://www.eatlas.idf.org/Prevaience/;2004.
2. American Diabetes Association. http://www.diabetes.org/type-1-diabetes/complications.jsp. 2005.
3. Brearley S, Shearman C P, Simms M H. Peripheral pulse palpation: an unreliable physical sign. Ann R Coll Surg Engl 1992; 74(3):169-71.
4. Frykberg R G, Lavery L A, Pham H, Harvey C, Harkless L, Veves A. Role of neuropathy and high foot pressures in diabetic foot ulceration. Diabetes Care 1998; 21(10):1714-9.
5. Sumpio B E. Foot ulcers. N Engl J Med 2000; 343(11): 787-93.
6. Young M J, Breddy J L, Veves A, Boulton A J. The prediction of diabetic neuropathic foot ulceration using vibration perception thresholds. A prospective study. Diabetes Care 1994; 17(6:557-60.
7. Cavanagh P, Young M, Adams J, al. e. Correlates of structure and function in neuropathic diabetic feet. Diabetologia 1991; 34(Suppl 2):A39 (abstract).
8. Lavery L A, Armstrong D G, Vela S A, Quebedeaux T L, Fleischli J G. Practical criteria for screening patients at high risk for diabetic foot ulceration. Arch Intern Med 1998; 158(2):157-62.
9. McMillan D E. Development of vascular complications in diabetes. Vasc Med 1997; 2(2):132-42.
10. Novo S. Classification, epidemiology, risk factors, and natural history of peripheral arterial disease. Diabetes Obes Metab 2002; 4 Suppl 2:S1-6.
11. Hittel N, Donnelly R. Treating peripheral arterial disease in patients with diabetes. Diabetes Obes Metab 2002; 4 Suppl 2:S26-31.
12. Pecoraro R E, Reiber G E, Burgess E M. Pathways to diabetic limb amputation. Basis for prevention. Diabetes Care 1990; 13(5):513-21.
13. Reiber G E, Boyko E J, Smith D C. Lower extremity foot ulcers and amputations in diabetes. In: Harris, Cowie, Stern, Boyko E J, Reiber G E, Bennet, editors. Diabetes in America. 2nd ed. Washington, D.C.: US Government Printing Office; 1995. p. 402-428.
14. Palumbo P J, Melton L J. Peripheral vascular disease and diabetes. In: Harris, Hamman, editors. Diabetes in America. 1st ed. Washington, D.C.: US Government Printing Office; 1985.
15. Frykberg R G, Armstrong D G, Giurini J, Edwards A, Kravette M, Kravitz S, et al. Diabetic foot disorders: a clinical practice guideline. American College of Foot and Ankle Surgeons. J Foot Ankle Surg 2000; 39(5 Suppl):S1-60.
16. Ramsey S D, Newton K, Blough D, McCulloch D K, Sandhu N, Reiber G E, et al. Incidence, outcomes, and cost of foot ulcers in patients with diabetes. Diabetes Care 1999; 22(3):382-7.
17. Harrington C, Zagari M J, Corea J, Klitenic J. A cost analysis of diabetic lower-extremity ulcers. Diabetes Care 2000; 23(9):1333-8.
18. Caputo G M, Cavanagh P R, Ulbrecht J S, Gibbons G W, Karchmer A W. Assessment and management of foot disease in patients with diabetes. N Engl J Med 1994; 331(13): 854-60.

19. Lavery L, Gazewood J D. Assessing the feet of patients with diabetes. J Fam Pract 2000; 49(11 Suppl):S9-16.
20. Frykberg R G. Diabetic foot ulcers: pathogenesis and management. Am Fam Physician 2002; 66(9):1655-62.
21. Sykes M T, Godsey J B. Vascular evaluation of the problem diabetic foot. Clin Podiatr Med Surg 1998; 15(1):49-83.
22. Treado P J, Morris M D. Infrared and Raman spectroscopic imaging. Appl Spectrosc Rev 1994; 29:1-38.
23. Riaza A, Strobl P, Muller A, Beisl U, Hausold A. Spectral mapping of rock weathering degrees on granite using hyperspectral DAIS 7915 Spectrometer Data. Internl J Applied Earth Observation and Geoinformation Special issue: Applications of imaging spectroscopy 2001; 3-4: 345-354.
24. Thenkabail P S, Smith R B, De Pauw E. Hyperspectral vegetation indices and their relationships with agricultural crop characteristics. Remote Sens Environ 2000; 71(REMOTE SENS ENVIRON):158-182.
25. Colarusso P, Kidder L H, Levin I W, et al. Infrared spectroscopic imaging: from planetary to cellular systems. Appl Spectrosc 1998; 52:106A-120A.
26. HyperMed, Inc., Issued U.S. Pat. Nos. 6,937,885; 6,810,279, 6,741,884; 6,640,130; and 6,640,132; and others pending.
27. Freeman J E, Shi Y, Panasyuk S V, Rogers A E. Medical hyperspectral imaging (MHSI) of 1,2-dimethylbenz(a)-anthracene (DMBA)-induced breast tumors in rats. Poster #1001. In: 27th Annual San Antonio Breast Cancer Symposium; 2004; San Antonio, Tex.: Breast Cancer Research and Treatment; 2004. p. S51.
28. Carlson K A, Jahr J S. A historical overview and update on pulse oximetry. Anesthesiol Rev 1993; 20:173-181.
29. Zuzak K J, Schaeberle M D, Gladwin M T, et al. Noninvasive determination of spatially resolved and time-resolved tissue perfusion in humans during nitric oxide inhibition and inhalation by use of a visible-reflectance hyperspectral imaging technique. Circulation 2001; 104: 2905-2910.
30. Afromowitz M A, Callis J B, Heimbach D M, DeSoto L A, Norton M K. Multispectral imaging of burn wounds: a new clinical instrument for evaluating burn depth. IEEE Trans Biomed Eng 1988; 35(10):842-50.
31. Sowa M G, Leonardi L, Payette J R, Fish J S, Mantsch H H. Near infrared spectroscopic assessment of hemodynamic changes in the early post-burn period. Burns 2001; 27:241-9. Burns 2001; 27:241-249.
32. Dinh T, Panasyuk S, Freeman J, Panasyuk A A, Lew R, Brand D, et al. Medical hyperspectral imaging (MHSI) evaluation of microcirculatory changes to predict clinical outcomes: Application to diabetic foot ulcers. Society of Vascular Medicine and Biology 17th Annual Scientific Session 2006: (Abstract submitted).
33. Dinh T, Panasyuk S V, Jiang C, Freeman J, Panasyuk A A, Nerney M, et al. The use of medical hyperspectral imaging (MHSI) to evaluate microcirculatory changes in diabetic foot ulcers and predict clinical outcomes. American Diabetes Association 66th Scientific Session 2006: (abstract accepted).
34. Dinh T, Panasyuk S V, Tracey B H, Khaodhiar L, Lyons T E, Rosenblum B L, et al. The use of medical hyperspectral imaging (MHSI) to identify patients at risk for developing diabetic foot ulcers. Diabetes 2005; 54(S1):A270.
35. Dinh T, Panasyuk S V, Tracey B H, Khaodhiar L, Lyons T E, Rosenblum B L, et al. The use of medical hyperspectral imaging (MHSI) to identify patients at risk for developing diabetic foot ulcers. American Diabetes Association 65th annual session 2005:Poster #1106-P, June.
36. Greenman R I, Panasyuk S, Wang X, Lyons T E, Dinh T, Longorio L, et al. Early changes in the skin microcirculation and muscle metabolism of the diabetic foot. Lancet 2005; 366: 1711-1718. Lancet 2005; 366:1711-1718.
37. Mansfield J R, Lew R A, Lewis E N, Freeman J E, Kellicut D, Sidawy A. Hyperspectral imaging of diabetic foot conditions. In: Eastern Analytical Society Meeting; 2003; Somerset, N.J.; 2003.
38. Freeman J E, Panasyuk S V, Hopmeier M J, Lew R A, Batchinski A I, Cancio L C. The evaluation of new methods of hyperspectral image analysis for the diagnosis of hemorrhagic shock, Poster #17. In: American Association for the Surgery of Trauma; 2005; 2005.
39. Gillies R, Freeman J E, Cancio L C, Brand D, Hopmeier M, Mansfield J R. Systemic effects of shock and resuscitation monitored by visible hyperspectral imaging. Diabetes Technol Therapeut 2003; 5(5):847-855.
40. Panasyuk S V, Freeman J E, Cooke W I, Hopmeier M J, Convertino V A. Initial demonstration in human subjects of medical hyperspectral imaging (MHSI) as a novel stand-off non-invasive method for diagnosing and measuring hemodynamic compromise, Poster #18. In: American Association for the Surgery of Trauma; 2005; 2005.
41. Payette J R, Sowa M G, Germscheid S L, Stranc M F, Abdulrauf B, Mantsch H H. Noninvasive diagnostics: predicting flap viability with near-IR spectroscopy and imaging. Am Clinical Laboratory 1999; 18:4-6.
42. Armstrong D G, Lavery L A. Predicting neuropathic ulceration with infrared dermal thermometry. J Am Podiatr Med Assoc 1997; 87(7):336-7.
43. Beckert S, Witte M B, Konigsrainer A, Coerper S. The Impact of the Micro-Lightguide O2C for the Quantification of Tissue Ischemia in Diabetic Foot Ulcers. Diabetes Care 2004; 27(12):2863-2867.
44. Rajbhandari S M, Harris N D, Tesfaye S, Ward J D. Early identification of diabetic foot ulcers that may require intervention using the micro lightguide spectrophotometer. Diabetes Care 1999; 22(8):1292-5.
45. Khan F, Newton D J. Laser Doppler imaging in the investigation of lower limb wounds. Int J Low Extrem Wounds 2003; 2(2):74-86.
46. Sheffield P J, Fife C E, Smith A P S. Laser Doppler Flowmetry. In: Wound Care Practice. Flagstaff, Ariz.: Best Publishing Company; 2004.
47. Wardlaw J M, Dennis M S, Warlow C P, Sandercock P A. Imaging appearance of the symptomatic perforating artery in patients with lacunar infarction: occlusion or other vascular pathology? Ann Neurol 2001; 50(2):208-15.
48. Zimny S, Dessel F, Ehren M, Pfohl M, Schatz H. Early detection of microcirculatory impairment in diabetic patients with foot at risk. Diabetes Care 2001; 24(10): 1810-4.

The invention claimed is:

1. A multispectral or hyperspectral medical imaging system comprising:
a plurality of LED lights, each respective LED light in the plurality of LED lights configured to emit radiation at a particular spectral band in a plurality of spectral bands used by a diagnostic protocol module;
a first stage optic configured to receive radiation projected, from one or more respective LED lights in the plurality of LED lights, off of an in vivo tissue located at a region of interest on a subject;
an imaging sensor for recording an image of the radiation projected off of the in vivo tissue;

a diagnostic protocol module adapted to detect a particular characteristic of the in-vivo tissue;

a diagnostic processor configured to:
- switch one or more respective LED light in the plurality of LED lights off and on based on the diagnostic protocol module,
- instruct the imaging sensor to record a plurality of images of the region of interest based on the diagnostic protocol module, each respective image in the plurality of images corresponding to radiation emitted at a particular spectral band by one or more respective LED light in the plurality of LED lights,
- co-register corresponding pixels in each image in the plurality of images;
- derive a coefficient for oxyhemoglobin and a coefficient for deoxyhemoglobin from each set of co-registered pixels in the plurality of images;
- generate, based on the plurality of images, a two-dimensional index characterizing the particular characteristic of the in vivo tissue, wherein the two-dimensional index includes a first scale to represent a concentration of oxyhemoglobin in the in vivo tissue, and a second scale to indicate a concentration of deoxyhemoglobin in the in vivo tissue;
- display the coefficient for oxyhemoglobin and the coefficient for deoxyhemoglobin from at least one set of co-registered pixels in the plurality of images independently with the two-dimensional index on a video display, thereby conveying spatial information about oxyhemoglobin concentration and deoxyhemoglobin concentration in the tissue.

2. The multispectral or hyperspectral medical imaging system of claim 1, wherein the imaging system is portable.

3. The multispectral or hyperspectral medical imaging system of claim 2, wherein the imaging system weighs less than 25 pounds.

4. The multispectral or hyperspectral medical imaging system of claim 1, wherein the plurality of LED lights is configured in a circular array about the first stage optic.

5. The multispectral or hyperspectral medical imaging system of claim 1, wherein at least one respective LED light in the plurality of LED lights is configured to emit radiation in the visible spectrum.

6. The multispectral or hyperspectral medical imaging system of claim 1, wherein at least one respective LED light in the plurality of LED lights is configured to emit radiation in the near-infrared spectrum.

7. The multispectral or hyperspectral medical imaging system of claim 5, wherein at least one respective LED light in the plurality of LED lights is configured to emit radiation in the near-infrared spectrum.

8. The multispectral or hyperspectral medical imaging system of claim 1, further comprising a first radiation filter placed in front of a respective LED light in the plurality of LED lights and a second, matching radiation filter, placed in optical communication with the imaging sensor.

9. The multispectral or hyperspectral medical imaging system of claim 1, further comprising one or more polarizers in optical communication with the first stage optic.

10. The multispectral or hyperspectral medical imaging system of claim 9, wherein a first polarizer in the one or more polarizers is placed in front of a respective LED light in the plurality of LED lights and a second polarizer in the one or more polarizers is placed in optical communication with the first stage optic.

11. The multispectral or hyperspectral medical imaging system of claim 1, wherein the imaging sensor is configured to detect radiation in the visible spectrum.

12. The multispectral or hyperspectral medical imaging system of claim 1, wherein the imaging sensor is configured to detect radiation in the near-infrared spectrum.

13. The multispectral or hyperspectral medical imaging system of claim 11, wherein the imaging sensor is configured to detect radiation in the near-infrared spectrum.

14. The multispectral or hyperspectral medical imaging system of claim 1, wherein the video display is contained within the multispectral or hyperspectral medical imaging system.

15. The multispectral or hyperspectral medical imaging system of claim 1, wherein the video display is not contained within the multispectral or hyperspectral medical imaging system.

16. The multispectral or hyperspectral medical imaging system of claim 1, further comprising a communication interface in electrical communication with the diagnostic processor.

17. The multispectral or hyperspectral medical imaging system of claim 1, wherein each respective spectral band in the plurality of spectral bands used by the diagnostic protocol module has a bandwidth of less than 20 nm.

18. The multispectral or hyperspectral medical imaging system of claim 1, wherein the diagnostic processor comprises a plurality of diagnostic protocol modules, each of which are adapted to detect a specific characteristic of the in vivo tissue.

19. The multispectral or hyperspectral medical imaging system of claim 1, wherein the first scale of the two dimensional index is a color scale and the second scale of the two dimensional index is a brightness scale.

20. The multispectral or hyperspectral medical imaging system of claim 1, further comprising an image projector.

21. The multispectral or hyperspectral medical imaging system of claim 1, further comprising a calibrator.

* * * * *